US011607384B2

(12) United States Patent
Prabhu et al.

(10) Patent No.: US 11,607,384 B2
(45) Date of Patent: Mar. 21, 2023

(54) LIPID EMULSIFIED DRUG DELIVERY SYSTEMS FOR CHEMOPREVENTION AND TREATMENT

(71) Applicant: WESTERN UNIVERSITY OF HEALTH SCIENCES, Pomona, CA (US)

(72) Inventors: Sunil Prabhu, Pomona, CA (US); Preshita Desai, Pomona, CA (US); Arvind Thakkar, Portland, ME (US)

(73) Assignee: WESTERN UNIVERSITY OF HEALTH SCIENCES, Pomona, CA (US)

( * ) Notice: Subject to any disclaimer, the term of this patent is extended or adjusted under 35 U.S.C. 154(b) by 0 days.

(21) Appl. No.: 16/770,374

(22) PCT Filed: Dec. 7, 2018

(86) PCT No.: PCT/US2018/064500
§ 371 (c)(1),
(2) Date: Jun. 5, 2020

(87) PCT Pub. No.: WO2019/113461
PCT Pub. Date: Jun. 13, 2019

(65) Prior Publication Data
US 2020/0383913 A1    Dec. 10, 2020

Related U.S. Application Data

(60) Provisional application No. 62/596,380, filed on Dec. 8, 2017.

(51) Int. Cl.
*A61K 9/107* (2006.01)
*A61K 31/4545* (2006.01)
*A61K 47/06* (2006.01)
*A61K 47/44* (2017.01)

(52) U.S. Cl.
CPC .......... *A61K 9/107* (2013.01); *A61K 31/4545* (2013.01); *A61K 47/06* (2013.01); *A61K 47/44* (2013.01)

(58) Field of Classification Search
CPC .............................. A61K 9/107; A61K 31/138
See application file for complete search history.

(56) References Cited

U.S. PATENT DOCUMENTS

| | | | | |
|---|---|---|---|---|
| 6,096,338 A | * | 8/2000 | Lacy ................. | A61K 9/48 424/455 |
| 6,635,654 B1 | * | 10/2003 | Chang ................. | A61K 31/44 514/290 |
| 2004/0092428 A1 | * | 5/2004 | Chen ................. | A61K 38/00 514/2 |
| 2012/0301544 A1 | | 11/2012 | Okutan et al. | |

FOREIGN PATENT DOCUMENTS

WO     WO2006107903 A2 * 10/2006    ............. C08G 65/00

OTHER PUBLICATIONS

NIH, National Cancer Institute, Risk Factors for Cancer, publication date: Dec. 23, 2015 (Year: 2015).*
Alex Kentsis, Why do young people get cancer?, Pediatr Blood Cancer. Jul. 2020; 67(7): e28335 (Year: 2020).*
ACS, The American Cancer Society medical and editorial content team, How Chemotherapy Drugs Work, downloaded in Oct. 2021 (Year: 2021).*
Aamer Qazi, Anticancer Activity of a Broccoli Derivative, Sulforaphane, in Barrett Adenocarcinoma: Potential Use in Chemoprevention and as Adjuvant in Chemotherapy, Translational Oncology, vol. 3, No. 6, 2010 (Year: 2010).*
International Search Report and Written Opinion in International Application No. PCT/US2018/065400, dated Feb. 22, 2019.
International Preliminary Report on Patentability in International Application No. PCT/US2018/064500, dated Jun. 18, 2020.
Castor Oil, Wikipedia, Dec. 4, 2017, p. 1-2 retrieved Feb. 5, 2019 via internet at https://en.wikipedia.org/w/index.php?title=Castor_oil &oldid=813621584.

* cited by examiner

*Primary Examiner* — Mark V Stevens
*Assistant Examiner* — Alparslan Asan
(74) *Attorney, Agent, or Firm* — Fox Rothschild LLP

(57) ABSTRACT

Disclosed herein are lipid emulsified systems containing antihistamines. Also disclosed herein are pharmaceutical compositions containing the lipid emulsified systems and other chemotherapeutic agents, and methods of chemoprevention and cancer treatment with compositions containing the lipid emulsified systems.

17 Claims, 8 Drawing Sheets

LIPID EMULSIFIED DRUG DELIVERY SYSTEMS FOR CHEMOPREVENTION AND TREATMENT

CROSS-REFERENCE TO RELATED APPLICATIONS

This application claims priority to U.S. Application Ser. No. 62/596,380, filed Dec. 8, 2017, which is hereby incorporated by reference in its entirety.

FIELD OF THE INVENTION

The invention relates to lipid emulsified systems, pharmaceutical compositions, and methods for the chemoprevention and treatment of cancer.

BACKGROUND

Pancreatic cancer is a highly aggressive form of cancer with 5 years of life expectancy in only about 8% patients. Pancreatic cancer is the fourth leading cause of deaths in the United States, projected to be second leading cause by 2025 after lung cancer. The median survival of metastatic pancreatic cancer patients is about 1 year or less when treated with first-line gold standard therapy of gemcitabine combinations and Folfirinox®. This confirms the inefficiency of the available drug therapy. The estimated prevalence of pancreatic cancer in the year 2017 is about 53,670 new cases with death of approximately 43,090 patients. It is, therefore, desirable to manage pancreatic cancer by prevention of pancreatic cancer using novel formulations for effective chemoprevention, and enhance therapeutic efficacy using novel supplement therapy that can potentiate effectiveness of existing treatments.

Ideally, a chemopreventive agent should have specific targets that are highly expressed in cancer cells or premalignant lesions but should not be expressed in normal tissue (Theo M. de Kok, et al., Eur J Nutr. 2008; 47: 51-59). The development of pancreatic cancer (PC) involves multiple pathways with various growth factors and several gene key regulators. Because of the heterogeneity and genomic instability of PC, a single therapeutic agent is often insufficient and the recurrent cancer is subsequently much harder to treat therapeutically. However, the use of a combination of different drugs that target multiple pathways has been considered as an effective strategy for cancer therapy. The combination of agents that affects multiple functional pathways may have the opportunity to generate additive or synergistic activity with less toxicity and increased efficacy. (Fazlul H. Sarkar, et al., Radiat Oncol. 2015; 10: 255; Sohn B S, et al., Oncol Lett. 2015; 10: 1204-1210.) Natural and synthetic compounds have both been evaluated as cancer chemopreventive agents. These compounds can either target a single specific pathway (synthetic compounds) or several pathways involved in carcinogenesis (mainly the natural compounds). (Wang Z, et al., Life Sci. 2008; 83: 293-300.) Gemcitabine and celecoxib are promising preventive agents known to reduce the risk of metastatic pancreatic adenocarcinoma cancer, but did not demonstrate significant improvement in measured clinical outcomes, in patients with advanced pancreatic cancer. Higher doses of celecoxib may be needed to observe significant antitumor activity. (Dragovich T, et al., Am J Clin Oncol. 2008; 31: 157-162; Noble S, et al., Drugs. 1997; 54: 447-472; Agnieszka Z. et al., Pharmacological Reports. 2012; 64: 1020-1037.) Recently, the strategy that combinational use with several chemopreventive agents at low doses induces greater inhibition of carcinogenesis has become the focus. Also, studies show the use of combinations of cisplatin, epirubicin, 5-fluorouracil and gemcitabine regimen for the treatment of patients with recurrent PC. Since these agents have different mechanisms of action in chemoprevention, a synergistic effect may be expected rather than single drug administration at higher levels. (Arvind Thakkar, et al., Oncol Rep. 2013; 29: 1671-1677.) Concomitantly, the use of combination therapy with different mechanisms of action provide brighter prospects in evaluating the combination of chemopreventive regimens with better efficacy and tolerability.

Classical anti-histaminics (loratadine (LOR) and desloratadine (DES)) are already approved by the U.S. Food and Drug Administration (FDA). Sulforaphane (SFN) is available as nutraceutical supplement. Numerous studies have suggested that antihistamines such as astemizole, terfenadine, diphenhydramine (H1 receptor antagonist) and cimetidine (H2 receptor antagonist) can reduce incidence and mortality of cancers such as melanoma, colorectal cancer and prostate cancer both in vitro and in vivo. (Steward, W. P. and K. Brown, Br J Cancer, 2013. 109(1): p. 1-7; Thakkar, A., et al., Int J Oncol, 2015. 46(4): p. 1827-34; Blaya, B., et al., Inflamm Allergy Drug Targets, 2010. 9(3): p. 146-57. In recent years, LOR, a well-known second-generation H1 histamine antagonist, has been reported to inhibit the growth of human colon cancer cells (COLO-2) due to both cell cycle arrests in G2/M phase and caspase 9-mediated apoptosis. LOR was discovered in 1981 and came to the market as an OTC drug in 1993. (Garcia-Quiroz, J. and J. Camacho, Anticancer Agents Med Chem, 2011. 11(3): p. 307-14; Jangi, S. M., et al., Carcinogenesis, 2006. 27(9): p. 1787-96; Matsumoto, S., et al. Br J Cancer 2002 Jan. 21 [cited 86 2]; 2002/03/01:[161-7]. LOR is metabolized rapidly to DES to provide its antihistamine activity. Sulforaphane is a naturally derived sulfur containing isothiocyanate derived from a family of compounds called glucosinolates, found in cruciferous vegetables such as broccoli, brussel sprouts, cauliflower and cabbage has been shown to possess potent chemopreventive activity. (Tortorella S M, et al., Antioxidant Redox Signal. 2015; 22: 1382-1424.).

It is expected that dosage amounts of the drugs, which are lower than approved prescription doses would not lead to any severe side effects. Antihistamines and sulforaphanes have also been evaluated as potential anticancer drugs. See Anne-Marie Ellegaard, et al., EBioMedicine. 9: 130-139. doi: 10.1016/j.ebiom.2016.06.013, and Vladimir J Lozanovski, et al., Trials. 2014; 15: 204. doi: 10.1186/1745-6215-15-204. However, these compounds, alone, do not offer sufficient anticancer efficacy for their clinical use.

SUMMARY OF THE INVENTION

The invention generally relates to methods and compositions for enhanced chemoprevention and enhanced therapeutic efficacy against cancer. In particular, the invention relates to lipid emulsified systems, pharmaceutical compositions, and methods for the prevention and treatment of cancer.

Lipid emulsified systems of the invention include (a) a lipid (b) a surfactant, (c) an antihistamine selected from LOR or des; (d) optionally a stabilizer; and (e) optionally, a cryoprotectant; where the average particle size of the lipid emulsified system is less than or equal to about 500 nm; where the ratio of (a) the lipid to (c) the antihistamine is about 4:1 to about 20:1; and where the ratio of (a) the lipid to (b) the surfactant is from about 1:1 to about 1:4.

Pharmaceutical compositions of the invention include lipid emulsified systems of the invention, and a pharmaceutically acceptable excipient. Some pharmaceutical compositions of the invention further comprise sulforaphane and/or an additional chemotherapeutic agent.

Methods of the invention include treating or preventing cancer in an individual in need thereof, and include the step of administering to the individual an effective amount of a pharmaceutical composition of the invention, where the cancer is selected from breast cancer, melanoma, ovarian cancer, lung cancer, pancreatic cancer, myeloma cancer, colorectal cancer, renal cancer, lymphoma and colon cancer.

Methods according to the invention also treat cancer in an individual in need thereof, where the cancer is at least in part resistant to treatment by a chemotherapeutic agent, and include a step of administering to the individual an effective amount of pharmaceutical compositions containing lipid emulsified systems of the invention, and optionally sulforaphane, in combination with the chemotherapeutic agent, where the cancer is selected from breast cancer, melanoma, ovarian cancer, lung cancer, pancreatic cancer, myeloma cancer, colorectal cancer, renal cancer, lymphoma and colon cancer.

DETAILED DESCRIPTION

Figure 1:
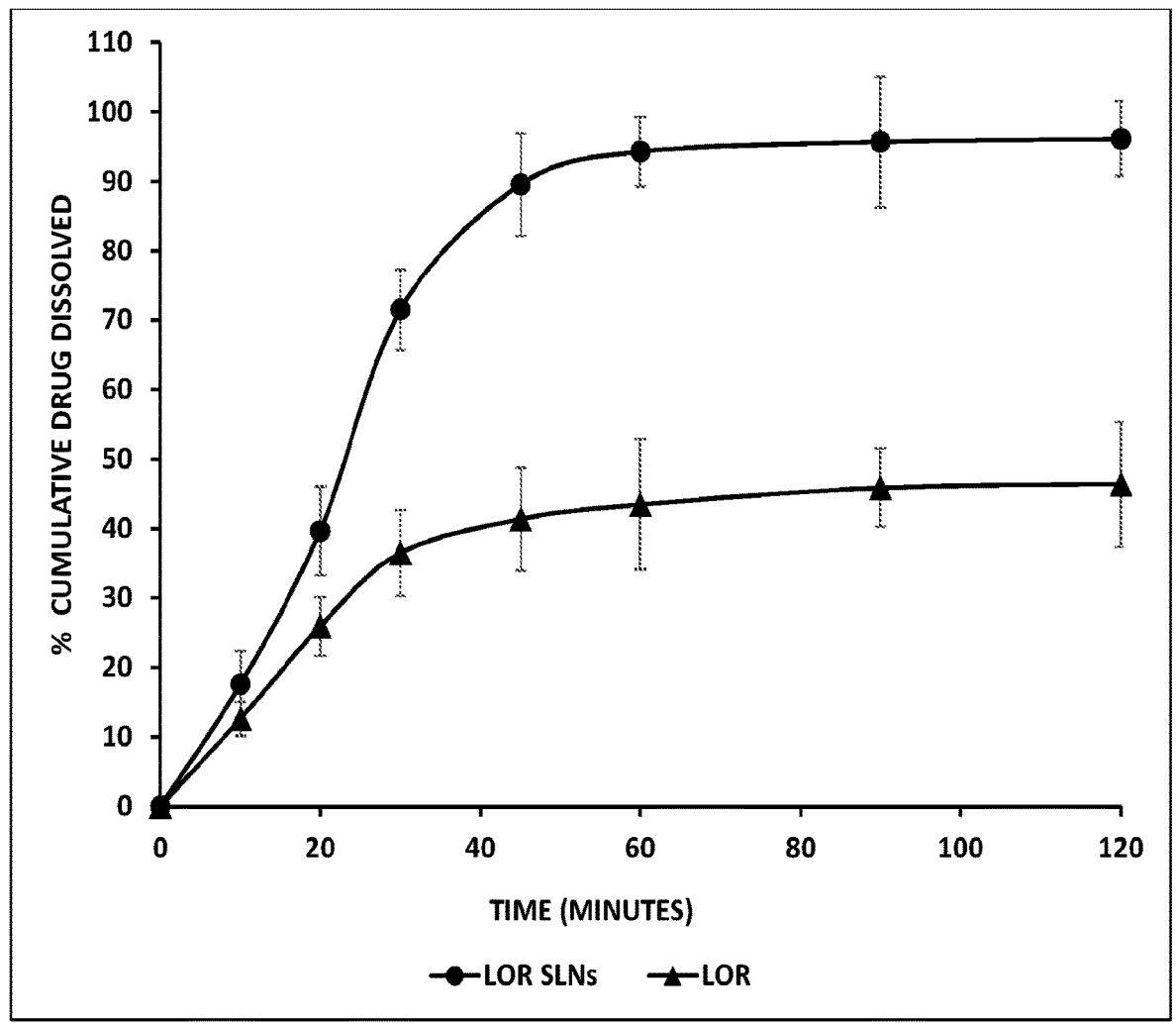
FIG. 1. shows the drug release profile of LOR from solid lipid nanoparticles of the invention.

The invention relates to lipid emulsified systems, pharmaceutical compositions, and methods for the prevention and treatment of cancer. Lipid emulsified systems of the invention incorporate LOR and DES active ingredients to provide enhanced bioavailability and enhance the ability of LOR and DES to kill cancer cells by several orders of magnitude, resulting in enhanced chemoprevention and enhanced treatment of cancer at very low doses relative to free drug. Lipid emulsified systems of the invention administered in combination with chemotherapeutic agents are useful in reducing the dose of the chemotherapeutic agent, thereby reducing potential side effects of the chemotherapeutic agent. Lipid emulsified systems of the invention administered in combination with chemotherapeutic agents are also useful in overcoming drug resistance to the chemotherapeutic agent.

Lipid emulsified systems of the invention comprise (a) a lipid (b) a surfactant, (c) an antihistamine selected from LOR or DES; (d) optionally a stabilizer; and (e) optionally, a cryoprotectant; wherein the average particle size of the lipid emulsified system is less than or equal to about 500 nm; wherein the ratio of (a) the lipid to (c) the antihistamine is about 4:1 to about 20:1; and where the ratio of (a) the lipid to (b) the surfactant is from about 1:1 to about 1:4.

Lipid-emulsified systems in the compositions according to the invention may be solid lipid nanoparticles (SLNs), nanostructured lipid carriers, or microemulsions and nano emulsions. SLNs are lipid nano emulsified systems wherein the lipids are solid lipids. Nanostructured lipid carriers are lipid nano emulsified systems wherein the lipids are mixture of solid lipids and liquid lipids (oils). Microemulsions and nanoemulsions are lipid nano emulsified systems wherein the lipids are liquid lipids (oils). Emulsions are fine dispersions of minute droplets of one liquid in another in which it is not soluble or miscible. Some lipid emulsified systems of the invention are microemulsions and nano emulsions containing lipid droplets or lipid globules in an aqueous medium.

Some lipid-emulsified systems according to the invention comprise solid and/or liquid lipids in combination with one or more surface active agents and/or stabilizers. The lipids used in the lipid-emulsified system are either solid lipids or liquid lipids (oils), which are known in the art. The lipids may be selected from fatty acids or mono- or di- or triglycerides, alone or in combination. The fatty acid chain length can vary from $C_6$-$C_{22}$ with or without unsaturation. For example, the fatty acid chains of the fatty acids or glycerides may be 6, 7, 8, 9, 10, 11, 12, 13, 14, 15, 16, 17, 17, 19, 20, 21, or 22 carbons in length. In a preferred lipid-emulsified system, the lipid is selected from the group consisting of stearic acid, oleic acid, glyceryl caprylate-caprate, and glyceryl monooleate, glyceryl dibehenate and combinations thereof. In a preferred lipid-emulsified system, the lipids are comprised of fatty acid and monoglycerides of $C_{18}$ saturated fatty acid chain, more preferably stearic acid, glyceryl mono-stearate. In another preferred lipid emulsified system, the lipids are mono-diglycerides of medium chain fatty acids, mainly caprylic and capric. More preferably, the lipid is selected from the group consisting of stearic acid, CAPMUL® MCM, CAPMUL® MCM C8, CAPMUL® GMO50, and combinations thereof. The CAPMUL® products are commercially available from ABITEC Corp., U.S.A. CAPMUL® MCM is a combination of glyceryl caprylate/caprate. CAPMUL® MCM C8 is a glyceryl caprylate oil. CAPMUL® GMO50 is a glyceryl mono-oleate.

Lipid-emulsified systems of the invention also comprise surfactants. The surfactant, as known in the art can selected from anionic, cationic or nonionic surfactants alone or in combinations thereof. In a preferred embodiment the surfactant is a nonionic surfactant. Preferably the nonionic surfactant is a polyoxypropylene-polyoxyethylene copolymer, a polyoxyethylene sorbitan ester of saturated or unsaturated fatty acids, a glyceryl ester of polyethylene glycols, or a combination thereof. More preferably, the surfactant is selected from the group consisting of Poloxamer® 188, Tween® 60, Tween® 80, Labrafil® M2125CS, and combinations thereof.

Lipid-emulsified systems of the invention optionally comprise a stabilizer. Stabilizers are surfactant and other agents, known in the art, that aid in the formation of, and further enhance or increase the stability of emulsions, but do not form an emulsion on their own without the presence of another surfactant. Preferably the stabilizer, when present, is a diethylene glycol monoethyl ether or a polyethylene glycol. More preferably, the stabilizer is selected from the group consisting of Transcutol® HP, PEG 200, and PEG 400.

Lipid-emulsified systems of the invention optionally comprise a cryoprotectant. The cryoprotectant if used in the formulation is an agent that protects the formulation from damage during freeze drying process. Cryoprotectants, as known in the art, may be selected from sugars, sugar alcohols, and polymers. Preferably the cryoprotectant is a sugar alcohol, more preferably mannitol.

In one embodiment, the lipid emulsified system is in the form of solid lipid nanoparticles. Lipid nanoparticles such SLNs are submicron sized colloidal particles with size range 50 to 1000 nm in diameter. In a lipid emulsified system of the invention, SLN are composed of physiologically tolerable lipids, surfactants and water. They remain solid at room temperature and contain hydrophilic shell and a hydrophobic core. Surfactants like poloxamer 188 and polyvinyl alcohol (PVA) are used to form hydrophilic shell and lipids such as stearic acid is used to form hydrophobic core. The active drug is added to the melted lipid (oil phase) and dispersed in aqueous phase containing surfactants (aqueous phase) to form stable emulsion. Surface modification of SLN can be used to overcome drug resistance in cancer chemotherapy, to achieve targeted delivery for better efficacy and reduced dose related toxicity. Moreover, they contain hydrophilic and hydrophobic surfactants as stabilizers, which have been reported to inhibit P-gp mediated drug efflux. (Melike Üner and Gülgün Yener, Int J Nanomedicine. 2007; 2: 289-300.) SLN systems can improve the aqueous solubility of poorly water-soluble drugs and provide controlled release of drug for longer period. The lipid core matrix of SLNs has been reported to stimulate chylomicron formation and facilitate lymphatic uptake, which can bypass hepatic first-pass drug metabolism. (Patricia Severino, et al., Journal of Drug Delivery. 2011; 10; Mehnert W, et al., Adv Drug Deliv Rev. 2001; 47: 165-196; Rawat M, et al., Biol Pharm Bull. 2006; 29: 1790-1798; Müller R H, et al., Eur J Pharm Biopharm. 2000; 50:161-177; Arvind Thakkar, et al., Cell Biosci. 2015; 5: 46; Yuan H, et al., Int J Pharm. 2008; 348: 137-145.) Thus, SLNs have attracted much interest as an oral delivery system for lipophilic drugs with poor bioavailability. To date, SLNs have been used successfully for enhancing the bioavailability of lipophilic drugs, such as cyclosporine A, paclitaxel, quercetin, vinpocetine and lopinavir. These characteristics make SLNs an attractive oral delivery system. (Kaushal P. Patel, et al., IJPSR. 2015; 6: 442-452; HouLi Lia, et al., Journal of Controlled Release. 2009; 133: 238-244; YiFan Luo, et al., Journal of Controlled Release. 2006; 114: 53-59; Baboota Sanjula, et al., Journal of Drug Targeting. 2009; 17: 249-256.) An important feature of SLN especially in the chemoprevention of PC is that they are absorbed via the lymphatic circulation thereby increasing the circulation time and bioavailability of drugs. This allows the administration of lower doses with fewer chances of toxic side effects, while maintaining their chemo preventive efficacy. (Nair R, et al., Lipids Health Dis. 2012; 11:72; Prakash Ramalingam, et al., Pharm Res. 2015; 32: 389-402.)

The lipid emulsified systems of the invention can be prepared by methods known in the art. For example, the systems may be prepared by a solvent emulsion evaporation method or a hot emulsification homogenization method. In one such hot emulsification homogenization method, drug, solid lipids in combination with one or more additional excipients from the class of surface-active agents and/or stabilizers are mixed in varied ratio and the mixture is melted to achieve homogeneous melt mix. After this, hot purified water is added drop by drop under homogenization and the system is cooled to room temperature to achieve a lipid emulsified system suspension. A varied concentration of cryoprotectant (1-5%) is added and the system is subjected to freeze drying to achieve dry powdered lipid emulsified system formulation. This formulation is stored as a dry lipid emulsified system. Prior to study, it is mixed with water under stirring to form a lipid emulsified system. In another hot emulsification homogenization method, drug, liquid lipids (oils) in combination with one or more additional excipients from the class of surface-active agents and/or stabilizers are mixed in varied ratio and the mixture is heated to achieve a homogeneous mix. This is stored as a preconcentrate lipid emulsified system. Prior to study, it is mixed with water under stirring to form a lipid emulsified system.

Lipid-emulsified systems in the compositions according to the invention may be solid lipid nanoparticles (SLNs), nanostructured lipid carriers, or microemulsions and nano emulsions. As used herein the term "average particle size of the lipid emulsified system" refers to the average particle size of the solid lipid nanoparticles, nanostructured lipid carriers, or the droplets or lipid globules formed within the microemulsion or nanoemulsion. A preferred lipid emulsified system of the invention is in the form of SLN. In this embodiment, the "average particle size of the lipid emulsified system" is the average particle size of the SLNs. Another preferred lipid emulsified system is a nanoemulsion. In this embodiment, the "average particle size of the lipid emulsified system" is the average particle size of the lipid droplets or lipid globules in an aqueous medium. When the lipid emulsified system of the invention is a microemulsion, the "average particle size of the lipid emulsified system" is the average particle size of the lipid droplets or lipid globules in an aqueous medium. When the lipid emulsified system of the invention is in the form of nanostructured lipid carriers, the "average particle size of the lipid emulsified system" is the average particle size of the nanostructured lipid carriers.

The average particle size of the lipid emulsified system can range from macro to nano scale but is preferred in nanoscale, more preferably, less than 500 nm, even more preferably less than 300 nm. For example, the average particle size of the lipid emulsified system is about 500 nm, about 450 nm, about 400 nm, about 350 nm, about 300 nm, about 250 nm, about 200 nm, about 150 nm, about 100 or less. Particle size may be measured by known methods in the art such as dynamic light scattering or photon correlation spectroscopy. Preferably, the particle size is measured by photon correlation spectroscopy using an instrument such as a Zetasizer (Nano ZS 90, Malvern Instruments, Malvern, UK). The average particle size, a.k.a. mean particle size, obtained through such measurements is also referred to as a Z-average. Polydispersity Index (PDI) is a measure of the width of the particle size distribution. Preferably, the PDI of the particle size distribution of lipid emulsified systems of the invention is 0.2 or less.

In lipid emulsified systems of the invention the antihistamine is selected from LOR or DES. Preferably the w/w ratio of the lipid to the antihistamine is from about 4:1 to about 20:1. In lipid emulsified systems of the invention, the w/w ratio of lipid to antihistamine is for example, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, or about 20:1. In lipid emulsified systems of the invention, the w/w ratio of lipid to surfactant is from about 1:1 to about 1:4, for example, 1:1, 1:2, 1:3, or 1:4.

Pharmaceutical compositions of the invention provide enhancement in chemopreventive action and therapeutic efficacy against cancer. Pharmaceutical compositions according to the invention comprise lipid-emulsified system formulations containing antihistamines LOR or DES as active ingredients, and a pharmaceutically acceptable excipient.

Depending on the type of pharmaceutical composition, the pharmaceutically acceptable excipient may be chosen from any one or a combination of excipients known in the art. The choice of the pharmaceutically acceptable excipient depends upon the pharmaceutical form and the desired method of administration to be used. The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference.

For example, pharmaceutical compositions can be prepared based on route of administration. Pharmaceutical compositions can be administered orally, parenterally, by inhalation spray, topically, rectally, nasally, buccally, vaginally or via an implanted reservoir. Parenteral, as used herein, includes subcutaneous, intracutaneous, intravenous, intramuscular, intraarticular, intraarterial, intrasynovial, intrasternal, intrathecal, intralesional, and intracranial injection or infusion techniques.

Injectable compositions can be prepared in conventional forms, either as liquid solutions or suspensions, solid forms suitable for solution or suspension in liquid prior to injection, or as emulsions. The injectables, solutions and emulsions may also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. SLNs can be incorporated in unit dosage forms such as capsule, tablet, and granules. Microemulsion/nanoemulsion preconcentrates can be incorporated in unit dosage forms such as soft gelatin capsules or can be adsorbed on inert excipients like sugars (lactose etc.), colloidal silicon dioxide (aerosol etc.) and the so formed solid formulations can then be incorporated into dosage forms such as capsules or tablets. The solid dosage forms so formed can also be provided as powders/granules such as sachets.

Examples of pharmaceutically acceptable excipients known in the pharmaceutical formulation art that may also be used in the pharmaceutical compositions of the invention include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, and antioxidants.

For a pharmaceutical composition of the invention, that is one having the lipid emulsified system of the invention, a carrier should be chosen that maintains the system. In other words, the excipient should not substantially alter the lipid emulsified system. Nor should the excipient be otherwise incompatible with the lipid emulsified system, such as by producing any undesirable biological effect or otherwise interacting in a deleterious manner with any other component(s) of the pharmaceutical composition.

Pharmaceutical compositions for enhanced chemoprevention and enhanced therapeutic efficacy, according to the invention, comprise lipid-emulsified system formulations LOR or DES, optionally in combination with sulforaphane and/or a chemotherapeutic agent. Some pharmaceutical compositions of the invention contain sulforaphane. Preferably, the ratio of LOR or DES to sulforaphane is about 25 to 1. Preferably, the sulforaphane is present in an amount which, as a free drug independent of lipid emulsified system, does not show significant cytotoxicity.

A chemotherapeutic agent is an chemical agent used to treat cancer, generally by directly killing cancer cells. Chemotherapeutic agents work by several mechanisms. In preferred pharmaceutical compositions of the invention, the chemotherapeutic agent is a nucleoside analog or antimetabolite, a mitotic inhibitor, a DNA alkylating or crosslinking agent, or enzyme modulator. Examples of nucleosides include gemcitabine and its derivatives, 5-fluorouracil, capecitabine, 6-mercaptopurine, and methotrexate. Examples of mitotic inhibitors include paclitaxel and docetaxel. Examples of DNA alkylating or crosslinking agents include cisplatin and oxaliplatin. Examples of enzyme modulators include: a topoisomerase I inhibitor, irinotecan; a topoisomerase II inhibitor, doxorubicin; a caspase inhibitor, baicalin; a selective estrogen receptor modulator, tamoxifen; a PARP inhibitor, olaparib; a COX-2 selective inhibitor, celecoxib; and a receptor tyrosine kinase inhibitor, elotinib. Preferably, the chemotherapeutic agent is selected from the group consisting of gemcitabine, paclitaxel, capecitabine, 5-fluorouracil, irinotecan, erlotinib, docetaxel, oxaliplatin, celecoxib, olaparib, tamoxifen, and doxorubicin. In particularly preferred pharmaceutical compositions, the chemotherapeutic agent is selected from paclitaxel and gemcitabine.

A method of preventing cancer, or chemoprevention, in an individual in need thereof according to the invention includes administering an effective amount of a pharmaceutical composition of the invention. Chemoprevention refers to the administration of agents that have the potential to prevent or delay the development of cancer. The cancer may be, for example, breast cancer, melanoma, ovarian cancer, lung cancer, pancreatic cancer, myeloma cancer, colorectal cancer, renal cancer, lymphoma and colon cancer, preferably pancreatic cancer. In preferred methods, the cancer is pancreatic cancer. Chemoprevention aims to prevent the development or recurrence of precancerous lesions and cancers with the use of natural or synthetic agents that reverse, suppress, delay, or prevent carcinogenic progression to invasive disease. Pancreatic cancer, for example, takes approximately 10 years to develop from the initial phase to a tumor and in the course of the disease it takes 5 more years to a metastatic spread. Boreddy et al., Cancer Lett., (2013), 334: 86-94. Chemopreventive agents are mainly used in individuals who are at high risk of developing cancer or who have had cancer or who have premalignant lesions. A cancer chemopreventive agent should be nontoxic to normal tissue so that it can be safely administered to cancer-free, at risk, or at high risk, individuals for a longer period.

Preferably, an individual in need of preventing cancer in methods of the invention is an individual who is at risk or at high risk of developing cancer. An individual at risk or at high risk may or may not have detectable disease, and may or may not have displayed detectable disease prior to the treatment methods described herein. "At risk or at high risk" denotes that an individual has one or more so-called risk factors, which are measurable parameters that correlate with development of cancer, for example pancreatic cancer. An individual having one or more of these risk factors has a higher probability of developing cancer than an individual without these risk factor(s). An "at high risk" individual has more factors or factors to a greater extent compared to an "at risk" individual. U.S. Pat. No. 9,820,949 discusses some of the risk factors for pancreatic cancer. Risk factors include, but are not limited to, age, sex, race, diet, smoking, alcohol consumption, history of previous pancreatic cancer, presence of hereditary pancreatic cancer syndrome, genetic considerations, and environmental exposure.

The pharmaceutical composition in a method according to the invention for chemoprevention is administered in an amount effective to prevent the development or recurrence of precancerous lesions and cancers or to reverse, suppress, delay, or prevent carcinogenic progression to invasive disease. Preferably, the pharmaceutical composition in a method according to the invention for chemoprevention is administered in an amount that is nontoxic to normal tissue so that it can be safely administered to cancer-free, at risk, or at high risk, individuals for a longer period of time.

A method of treating cancer to an individual in need thereof, according to the invention includes administering an effective amount of a pharmaceutical composition of the invention. The cancer may be, for example, breast cancer, melanoma, ovarian cancer, lung cancer, pancreatic cancer, myeloma cancer, colorectal cancer, renal cancer, lymphoma and colon cancer, preferably pancreatic cancer. As used herein, "treatment" or "treating" is an approach for obtaining beneficial or desired results including clinical results. For methods for treatment according to the invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer. The methods of the invention contemplate any one or more of these aspects of treatment.

In some methods of the invention for treating cancer, the pharmaceutical composition comprises a lipid emulsion system of the invention, and sulforaphane, and another chemotherapeutic agent. In another method of the invention for treating cancer, the pharmaceutical composition comprises a lipid emulsion system of the invention, and sulforaphane. In yet another of the invention for treating cancer, the pharmaceutical composition comprises a lipid emulsion system of the invention and sulforaphane, and another chemotherapeutic agent is administered with the pharmaceutical composition. In some methods, administration of the chemotherapeutic agent is concurrent with the pharmaceutical composition comprising a lipid emulsion system of the invention and sulforaphane. Concurrent administration means that the administrations overlap with each other. In other methods, the administration is sequential.

An effective amount in methods of treatment of the invention refers to an amount of a compound or composition sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation in pancreatic cancer. In some embodiments, an effective amount is an amount sufficient to delay or stop/prevent development of pancreatic cancer. In some embodiments, an effective amount is an amount sufficient to prevent or delay recurrence. An effective amount can be administered in one or more administrations. For example, in the case of pancreatic cancer, the effective amount of the drug or composition may: (i) reduce the number of pancreatic cancer cells; (ii) reduce tumor size; (iii) inhibit, retard, slow to some extent and preferably stop pancreatic cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; (vii) relieve to some extent one or more of the symptoms associated with pancreatic cancer; and/or (viii) disrupting (such as destroying) pancreatic cancer stroma.

One aspect of treatment is decreasing the dose of one or more other medications required to treat the disease. A method of treatment of the invention includes administering, to an individual in need of cancer treatment receiving a chemotherapeutic agent, a pharmaceutical composition comprising a lipid emulsified system of the invention, with or without sulforaphane, to reduce the dose of chemotherapeutic agent. Reduction in the dose of chemotherapeutic agent reduces potential side effects caused by the chemotherapeutic agent. Administering pharmaceutical compositions comprising lipid emulsified systems of the invention with or without sulforaphane, concurrently, with existing chemotherapeutic agent act to synergistically enhance and potentiate the therapeutic efficacy of existing drug therapy. Examples 9 and 10 show synergistic anticancer effects when pancreatic cell lines were treated with the combination regimens. Moreover, the combination with lipid emulsified system 2 and sulforaphane provides nearly 2×-3× increased efficacy compared to gemcitabine, alone, and the combination with lipid emulsified system 2 and sulforaphane provides nearly 2× increased efficacy compared to paclitaxel, alone.

Another method of the invention is a method of treating cancer in an individual in need thereof, wherein the cancer is at least in part resistant to treatment by a chemotherapeutic agent, comprising administering to the individual an effective amount of the pharmaceutical composition comprising lipid emulsified systems of the invention with or without sulforaphane, in combination with the chemotherapeutic agent. The cancer is selected from breast cancer, melanoma, ovarian cancer, lung cancer, pancreatic cancer, myeloma cancer, colorectal cancer, renal cancer, lymphoma and colon cancer, preferably pancreatic cancer. As shown in Example 9 and 10, the cell lines are more sensitive to the chemotherapeutic agents when combined with lipid emulsified systems of the invention and sulforaphane. The increased sensitivity of cancer cell lines to chemotherapeutic agents also allows for the use of the combination treatment to be used against cancers resistant to the chemotherapeutic agent. See, for example, Vadlapatla R K, Pal D, Vadlapudi A D Mitra A K (2014) Ritonavir: A Powerful Boosting Agent for Overcoming Drug Resistance in Cancer Chemotherapy. J Cancer Sci Ther 6:446-454. doi:10.4172/1948-5956.1000307 (https://www.omicsonline.org/open-access/ritonavir-a-powerful-boosting-agent-for-overcoming-drug-resistance-in-cancer-chemotherapy-1948-5956.1000307.php?aid=32839) (noting that due to results showing that ritonavir enhanced the ability of chemotherapeutics to inhibit cell growth "its repositioning in cancer chemotherapy may provide an excellent platform to reverse and overcome drug resistance besides providing enhanced antitumor efficacy."); https://www.cancer.gov/about-cancer/treatment/research/drug-combo-resistance ("Researchers believe one possible way to overcome or delay the development of resistance is to treat patients with combinations of different drugs. One combination treatment approach is to "co-administer drugs that work by different molecular mechanisms," Bissan Al-Lazikani, Ph.D., of Cancer Research UK and her colleagues wrote in Nature Biotechnology, "thereby increasing tumor cell killing while reducing the likelihood of drug resistance and minimizing overlapping toxicity.")

EXAMPLES

Materials

Chemicals and Reagents

For the cell culture assays and SLN formulations, the chemopreventive drugs DES was obtained from LKT laboratories (St. Paul, Minn.), LOR was from Tokyo Chemical Industry TCI (Tokyo, Japan) and SFN was obtained from SantaCruz Biotechnology (SantaCruz, Calif.). Dimethyl sulfoxide (DMSO) and acetic acid were obtained from Sigma Chemicals. Stearic acid (lipid) and Poloxamer 188 (emulsion stabilizer) were obtained from Spectrum Chemicals (Garden, Calif.). Labrafil® M2125CS, Transcutol® HP and Compritol was obtained from Gattefosse (Paramus, N.J.) and Tripalmitin was purchased from Sigma-Aldrich (WGK Germany). Capmul MCM, Capmul MCM C8, and Capmul GMO50 were purchased from Abitech Corp. U.S.A. Oleic acid, Tween 60 and Tween 80 were purchased from Sigma Inc. U.S.A. Dichloromethane (DCM) was obtained from Fisher Scientific (Houston, Tex.). Solvents like ethanol and ethyl acetate was obtained from VWR international (Darmstadt, Germany). For HPLC method, HPLC grade acetonitrile solvent were obtained from BDH Chemicals (Gibbstown, N.J.). Biotech Cellulose Ester Dialysis Membrane was purchased from Spectra/Por®.

Pancreatic Cancer Cell Lines

Human PC cells MIA PaCa-2 and Panc-1 were obtained from American type culture collection (ATCC) (Rockville, Md.). Cells were maintained in Dulbecco's modified Eagle's medium (DMEM) containing 10% fetal bovine serum (FBS) obtained from ATCC. Cells were cultured at 37° C. in a humidified atmosphere of 5% $CO_2$ and 95% air.

Example 1 Solid Lipid Nanoparticles

Preparation of Solid Lipid Nanoparticles

Solid Lipid Nanoparticles (SLNs) of LOR and DES were prepared using the hot homogenization process and single emulsification process. Optimization of the process was performed by varying process parameters including concentration of the lipid to drug, concentration of the surfactant, and different type of surfactants and solvents.

Two methods were explored for preparation of SLNs namely solvent emulsion evaporation and hot emulsification homogenization. For the solvent emulsion evaporation method, two different lipid materials (Stearic acid and Compritol) in combination with three different organic solvents (ethanol, DCM, and ethyl acetate) and poloxamer 2% as stabilizer were mixed in increasing drug to lipid ratios (1:2, 1:4, and 1:6) Various formulations were developed by changing one parameter at a time while keeping the other parameters constant (formulation F1-F8). The various formulations developed are listed in in Table 1.

TABLE 1

Development and optimization of various formulation parameters for SLNs

| Lipid | Solvent | Surfactant (2%) | Drug/lipid ratio | Formulation # | Particle size (nm) | | Polydispersity Index (PDI) | |
|---|---|---|---|---|---|---|---|---|
| | | | | | Agent 1 | Agent 2 | Agent 1 | Agent 2 |
| Stearic Acid | Ethanol | Poloxamer | 1:2 | F1 | 585 | 507 | 0.5 | 0.7 |
| | | | 1:4 | F2 | 487 | 469 | 0.6 | 0.6 |
| | | | 1:6 | F3 | 1217 | 925 | 0.8 | 0.9 |
| | DCM | Poloxamer | 1:2 | F4 | 486 | 382 | 0.4 | 0.3 |
| | | | 1:4 | F5 | 407 | 406 | 0.4 | 0.3 |
| | | | 1:6 | F6 | 677 | 992 | 0.9 | 0.5 |
| | Ethyl Acetate | Poloxamer | 1:2 | F7 | 657 | 872 | 1 | 0.9 |
| | | | 1:4 | F8 | 885 | 1007 | 0.9 | 0.9 |
| | | | 1:6 | F9 | Not forming emulsion | | | |

TABLE 1-continued

Development and optimization of various formulation parameters for SLNs

| Lipid | Solvent | Surfactant (2%) | Drug/lipid ratio | Formulation # | Particle size (nm) Agent 1 | Particle size (nm) Agent 2 | Polydispersity Index (PDI) Agent 1 | Polydispersity Index (PDI) Agent 2 |
|---|---|---|---|---|---|---|---|---|
| Compritol | Ethanol | Poloxamer | 1:2 | F10 | 447 | 421 | 0.3 | 0.3 |
|  |  |  | 1:4 | F11 | 392 | 408 | 0.2 | 0.4 |
|  |  |  | 1:6 | F12 | 695 | 581 | 0.6 | 0.6 |
|  | DCM | Poloxamer | 1:2 | F13 | 508 | 765 | 0.5 | 0.7 |
|  |  |  | 1:4 | F14 | 893 | 1042 | 0.8 | 0.8 |
|  |  |  | 1:6 | F15 | Not forming emulsion, drug came out of the solution while cooling down | | | — |
|  | Ethyl Acetate | Poloxamer | 1:2 | F16 | | | | |
|  |  |  | 1:4 | F17 | | | | |
|  |  |  | 1:6 | F18 | | | | |

A summary of all the formulations with their respective preparation conditions and characterization is presented in Table 1. LOR/DES SLNs were prepared using stearic acid and compritol as a lipid with drug to lipid ratio of 1:2, 1:4, or 1:6 with 2% Poloxamer as stabilizing aqueous phase. SLNs showed higher stability and lower particle size at low drug to lipid ratio (1:2 and 1:4), as shown in Table 1. It was observed that the mean particle diameter (z-average) of LOR/DES SLNs decreased with an increase in lipid concentration. Increases in lipid concentrations resulted in smaller particle size. However, as the lipid concentration increased from 1:4 to 1:6, the particle size of SLNs increased from around 400 nm to more than 600 nm or 800 nm in some formulations with high tendency to precipitate or agglomerate (F3, F8 and F14) as shown in Table 1.

The organic solvent is used during the solvent emulsion evaporation method to dissolve the drugs and lipids. Three different solvents, ethanol, dichloromethane and ethyl acetate were used in this study in varying volumes. The change in solvent had significant effect on the particle size as shown in Table 1. Among the solvents, ethanol was more compatible with the drugs and it dissolves the drug and lipid more readily. At higher concentration of lipid, ethyl acetate caused the drug to precipitate out of the formulation and was not able to form a stable emulsion. In particular, use of ethyl acetate with compritol did not form SLN formulation due to precipitations of solid even at low lipid concentration. The formulations using ethanol as a solvent resulted in lower particle size (400-650) and PDI (F1, F2, F10, and En) compared to those of DCM (800-1000 nm) and ethyl acetate. The formulation using ethyl acetate showed precipitation of particles (F15-F18).

Hot emulsification homogenization method: LOR/DES and stearic acid lipid were mixed with varied ratio of surfactants and the mixture was melted at 70° C. to achieve homogeneous melt mix. After this, purified water (70° C.) was added drop by drop under homogenization and the system was cooled to room temperature to achieve SLNs suspension. A varied concentration of mannitol (1-5%) was added as an cryoprotectant and the system was subjected to freeze drying to achieve dry powdered SLN formulation.

For further development of LOR/DES SLNs using the hot emulsification homogenization method, multiple surfactants such as tween 80, Transcutol HP (T-HP), and sodium deoxycholate were used during the optimization study. The type and concentration of surfactant affected the particle size, charge, as well as stability of NPs. The effect of three different surfactants on particle size and PDI is shown in Table 2.

TABLE 2

Development and optimization of various formulation parameters for SLNs with multiple surfactants

| Lipid | Lipid Ratio | Surfactant Ratio Tween 80 | Surfactant Ratio T-HP | Surfactant Ratio Sodium Deoxycholate | Formulation # | Particle size (nm) Agent 1 | Particle size (nm) Agent 2 | Polydispersity Index (PDI) Agent 1 | Polydispersity Index (PDI) Agent 2 |
|---|---|---|---|---|---|---|---|---|---|
| Stearic Acid | 1 | 1 | 1 | 0 | F19 | 265 | 286 | 0.2 | 0.2 |
|  | 1 | 1 | 0 | 1 | F20 | 547 | 682 | 0.4 | 0.5 |
|  | 1 | 2 | 1 | 0 | F21 | 986 | 1287 | 0.6 | 0.6 |
|  | 1 | 2 | 0 | 1 | F22 | 1142 | 959 | 1 | 1 |

Overall, the formulation using tween 80 and T-HP with the ratio of 1:1, respectively, gave the best SLNs in terms of size and polydispersity index (PDI). The measurements of particle sizes using the Zetasizer were 265 nm and 286 nm for LOR and DES SLNs, respectively with the PDI of 0.2 for both formulations. From the studies, hot emulsification homogenization method was selected as an optimum method owing to ease of formulation and stability and uniformity of formed SLNs. These optimized SLN formulation were considered optimum and were used for further studies.

Characterization of Solid Lipid Nanoparticles

The mean particle size (z-average) and PDI as a measure of the width of particle size distribution was determined by photon correlation spectroscopy using Zetasizer (Nano ZS 90, Malvern Instruments, Malvern, UK) at 25° and 90° scattering angle. Briefly, 5 mg of the SLN formulation was suspended in 10 ml of phosphate saline buffer (PBS and pH 7.4) and was sonicated for 30 seconds. Particle size was measured using 1 ml of the suspension. The surface charge was assessed by measuring zeta potential of SLNs based on the Smoluchowski Equation, using the same equipment at 25° C. with electric field strength of 23 V/cm. The formulated SLNs (F19) of LOR and DES had a mean particle size of 265±33 nm and 286±49 nm, with encapsulation efficiencies of 62% and 68%, respectively. The zeta potentials of LOR and DES SLNs were +21 mV and +15 mV, respectively.

To determine the encapsulation efficiency (% E.E) of the drug within the SLNs, the drugs were extracted from the nanoparticle lipid matrix by dissolving 10 mg of the SLN formulation in ethanol which dissolves the stearic acid and releases the drug entrapped within the lipid. Ethanol was evaporated under a current of inert air for 1 hour. Evaporation of ethanol left a residue of the drug and lipid sticking to the bottom of the test tube. Drug was separated from the lipid by dissolving it in 5 ml of acetonitrile. The drug was allowed to dissolve freely for about 30 minutes in a bath sonicator after which it was filtered through a 0.45 μm filter. The resulting solution was further diluted to 20 ml by adding acetonitrile. 1 ml of the resulting mixture was analyzed using Shimadzu LC-20 binary HPLC system (Columbia, Md.). 20 μl of caffeine was used as an internal standard. E.E was calculated using the following expression:

E.E (%)=Amount (mg) of drug per HPLC method/theoretical yield (mg)×100

HPLC quantitative analysis of LOR and DES were analyzed using a Shimadzu LC-20 binary HPLC system (Columbia, Md., USA). The % EE of LOR and DES SLNs were 62% and 68%, respectively.

Figure 2:
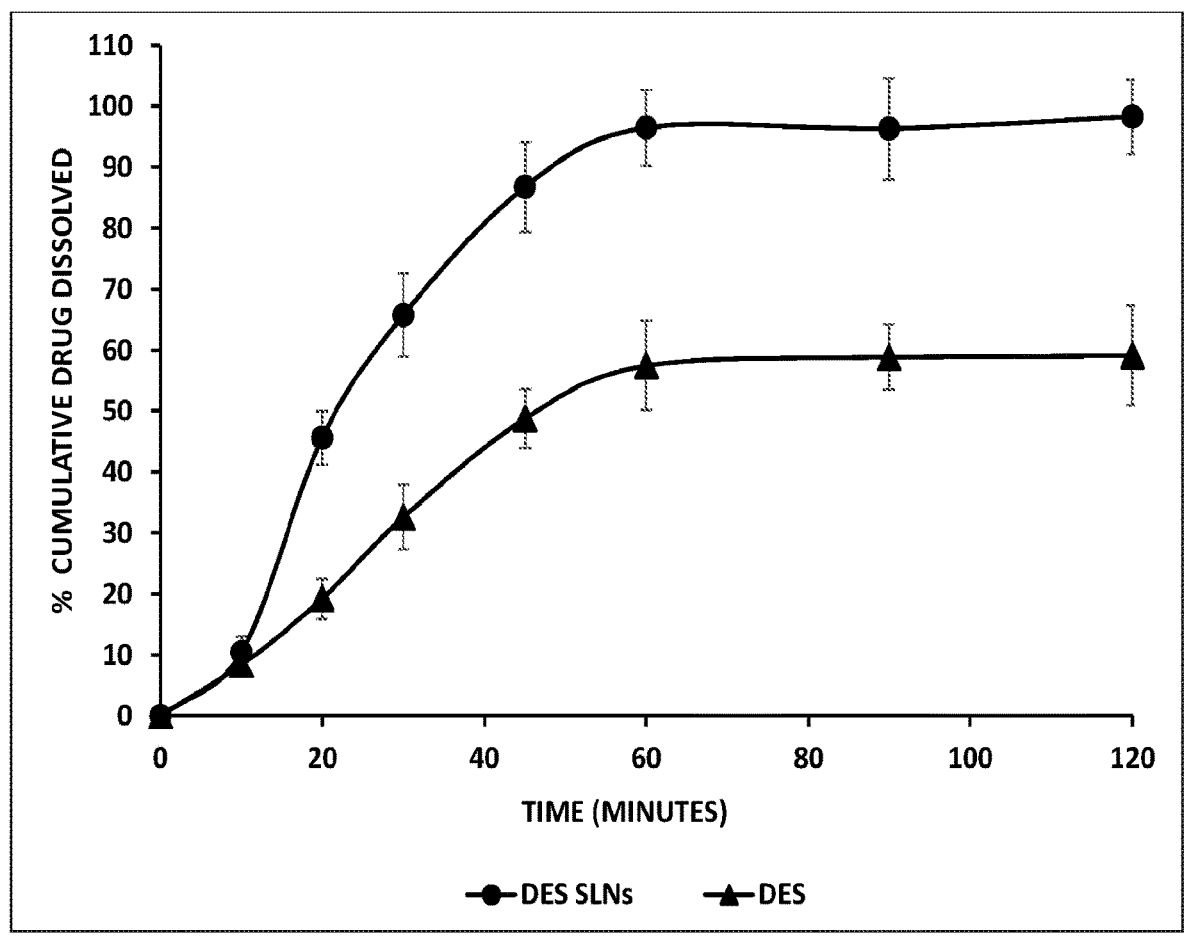
FIG. 2 shows the drug release profile of DES from solid lipid nanoparticles of the invention.

The cumulative release of LOR and DES were determined in 0.1N HCl 500 buffer solution, pH 7.4. SLN formulations containing 10 mg of drug was filled in a dialysis bag which was suspended in 500 ml of buffer at 37° C. with a stirring speed of 100 rpm. At predetermined time intervals up to 2 hours, 1 ml of the buffer was withdrawn and replaced with equivalent volume of fresh buffer. All samples are centrifuged at 5,000 rpm for 10 min. Supernatant was analyzed for drug release using HPLC. The analysis was carried out in triplicate Drug release studies of SLNs were performed using membrane compartmental analysis. The ability of LOR and DES SLNs to deliver drugs was examined by determined the drug release profiles, as shown in FIG. 1, FIG. 2, respectively. The percentage of drug released was plotted as a function of time. The SLNs exhibited an exponential drug release reaching plateau within 1 hour. The cumulative drug release of approximately 95% for both LOR and DES SLNs were observed within 1 hour of the study. After 2 hours, almost 100% of the drug encapsulated in the SLNs was released. In vitro drug release of LOR and DES from SLNs showed more than 90% of release within the first hour over 2-hour study period, demonstrating a slow and sustained release behavior.

The stability of drug loaded nanoparticles was performed to assess the stability of lyophilized SLNs LOR and DES as per ICH guidelines. The samples were stored at 2-8° C., 25° C. at 60% RH and 40° C. at 75% RH. For this study, all the formulations were packed in plain sealed bottles. The formulations were analyzed for particle size, PDI, encapsulation efficiency and in vitro drug release at evaluation time points. All the formulations were observed to be stable at refrigeration conditions as per the ICH Guidelines, however showed particle size increase at higher temperatures. See Table 3.

TABLE 3

Stability study LOR/DES SLNs

| | LOR SLN | | | | DES SLN | | | |
|---|---|---|---|---|---|---|---|---|
| Temp ° C. | Particle size (nm) | Zeta Potential (mV) | PDI | % EE | Particle size (nm) | Zeta Potential (mV) | PDI | % EE |
| 0 Day | | | | | | | | |
| 25° C./60% RH | 265 | 21 | 0.2 | 62 | 286 | 15 | 0.2 | 68 |
| 15 Day | | | | | | | | |
| 5 ± 3° C. | 302 | 21 | 0.2 | 62 | 316 | 16 | 0.3 | 68 |
| 25° C./60% RH | 401 | 21 | 0.2 | 60 | 407 | 16 | 0.3 | 68 |
| 40° C./75% RH | 1023 | 23 | 0.4 | 60 | 1150 | 20 | 0.4 | 67 |
| 30 Day | | | | | | | | |
| 5 ± 3° C. | 309 | 25 | 0.3 | 55 | 328 | 21 | 0.3 | 60 |
| 25° C./60% RH | 492 | 21 | 0.3 | 56 | 572 | 20 | 0.3 | 62 |
| 40° C./75% RH | 1317 | 28 | 0.7 | 50 | 1927 | 23 | 0.6 | 51 |

For (F19) LOR/DES SLNs, the mean size at the start of the storage study was 265 nm and 286 nm, respectively. At the end of 1 month, the particle size was 492, and 1317 nm at 25° C. and 40° C. for LOR SLNs and 572, and 1927 nm at 25° C. and 40° C. for DES SLNs. There was no observable change in zeta potential however % EE decreased at 40° C. for both formulations. Thus, % EE decreased while the particle size increased significantly at 25° C. and 40° C. for both LOR/DES SLNs. Accordingly, refrigeration is recommended for the F19 formulations. Based on the particle size and PDI values, stearic acid in combination with tween 80 and T-HP at 1:1:1 ratio, F19, was selected as optimal formulation and used for further studies.

Cytotoxicity Assays of LOR and DES SLNs

Figure 3:
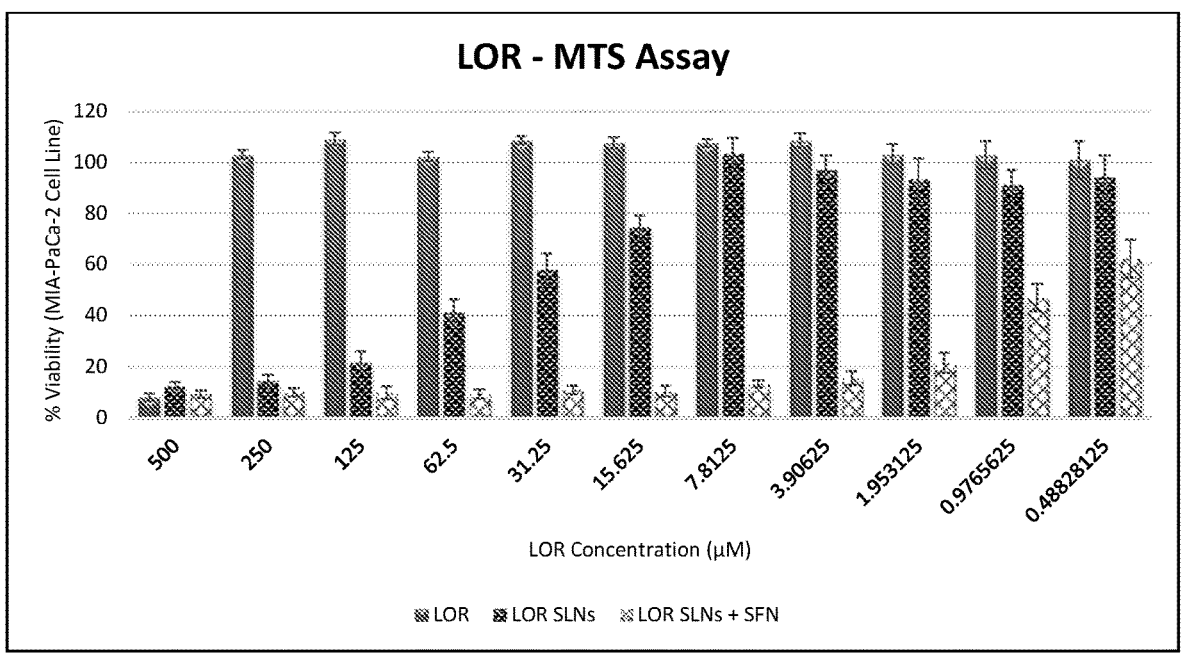
FIG. 3 shows cell viability in pancreatic cancer cells treated with LOR solid lipid nanoparticles of the invention at different concentrations. Abbreviation: LOR, Loratadine; SLNs, solid lipid nanoparticles. MTS assay was performed to determine the cell viability of Panc-1 and MIA PaCa-2 cells after treating with a range of concentrations of LOR SLNs for 72 h. The $IC_{50}$ values were then determined using nonlinear regression using graph pad prism software.
Figure 4:
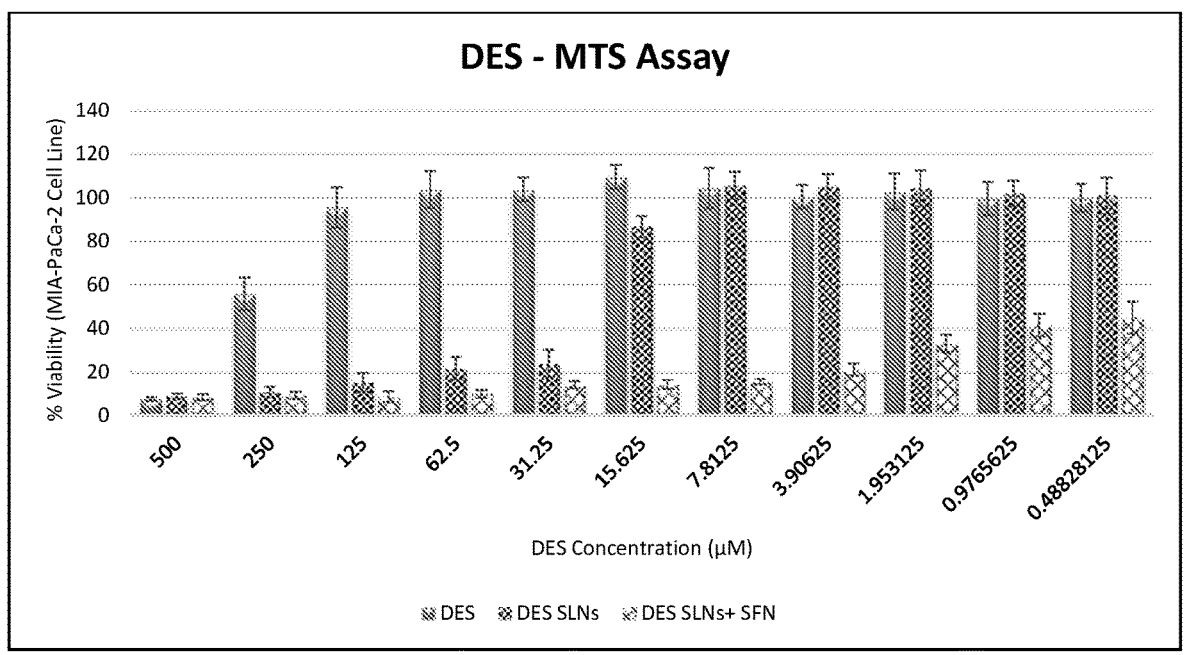
FIG. 4 shows cell viability in pancreatic cancer cells treated with DES solid lipid nanoparticles of the invention at different concentrations. Abbreviation: DES, Desloratadine; SLNs, solid lipid nanoparticles. MTS assay was performed to determine the cell viability of Panc-1 and MIA PaCa-2 cells after treating with a range of concentrations of DES SLNs for 72 h. The $IC_{50}$ values were then determined using nonlinear regression using graph pad prism software.

The cytotoxicity of LOR and DES loaded SLNs alone and in combination with SFN to the Panc-1 and MIA PaCa-2 were evaluated using a colorimetric MTS assay. The cell viability assay was performed according to manufacturer's protocol with the Promega CellTitre 96 Aqueous MTS reagent (Madison, Wis., USA). Briefly, 7.5×10³ cells were seeded in 96-well plates and incubated overnight. The cells were treated with different concentrations (500, 250, 125, 62.5, 31.25, 15.60, 7.80, 3.90, 1.95, 0.98, and 0.5 μM) of NPs (blank, LOR and DES SLNs) and incubated for a period of 72 hours. At the end of the incubation period, the growth medium was removed followed by addition of 100 μl media consisting of 20% MTS and 1% of phenazine methosulfate (PMS) and the mixture was incubated for 2 h at 37° C. MTS is bio-reduced by the cells into formazan which could be measured using a microplate reader at 490 nm. Thus, the quantity of formazan product measured by absorbance is directly proportional to the number of living cells in culture. $IC_{50}$ values were determined using Graph Pad Prism software (San Diego, Calif., USA). All analysis was performed in triplicate and replicated. Results are shown in FIG. 3 and FIG. 4.

Example 2: Cytotoxicity Assays with Lipid Emulsified Systems

A study to determine $IC_{50}$ (inhibitory concentration to kill 50% of cancer cells) in in vitro cell line cultures of pancreatic cancer cell line was performed. MIA-PaCa-2 pancreatic cancer cell line was incubated with varied concentration of LOR and DES alone or encapsulated within lipid emulsified system (Formulations 1-4) and in combination with fixed concentration of free SULFORAPHANE (5 μM) ((Formulations 5-8) for 72 h. $IC_{50}$ concentration was determined using MTS assay.

Formulation 1, Formulation 3, Formulation 5, and Formulation 7 were prepared as Lipid emulsified system 1: the lipid-emulsified system comprising solid lipids in combination with one or more additional excipients from the class of surface active agents and/or stabilizers. These formulations have the same component ratios as SLN formulation F19. For lipid emulsified system 1, drug, solid lipids in combination with one or more additional excipients from the class of surface active agents and/or stabilizers were mixed in varied ratio and the mixture was melted to achieve homogeneous melt mix. After this, hot purified water was added drop by drop under homogenization and the system was cooled to room temperature to achieve lipid emulsified system 1 suspension. A varied concentration of cryoprotectant (1-5%) was added and the system was subjected to freeze drying to achieve dry powdered lipid emulsified system 1 formulation. This was stored as a dry lipid emulsified system 1. Prior to study, it was mixed with water under stirring to form lipid emulsified system 1.

Formulation 2, Formulation 4, Formulation 6, and Formulation 8 were prepared as lipid emulsified system 2: the lipid-emulsified system comprising liquid lipids (oils) in combination with one or more additional excipients from the class of surface active agents and/or stabilizers. These formulations have the same lipid to surfactant ratios as formulation F19, except that mono-diglycerides of medium chain fatty acids (mainly caprylic and capric) was used as the liquid lipid, instead of stearic acid in F19. Capmul® MCM NF, a caprylic/capric mono-diglyceride, was purchased from ABITEC Corp. The lipid-emulsified system exhibited a particle size less than 500 nm. For lipid emulsified system 2, drug, liquid lipids (oils) in combination with one or more additional excipients from the class of surface-active agents and/or stabilizers were mixed in varied ratio and the mixture was heated to achieve homogeneous mix. This was stored as a preconcentrate lipid emulsified system 2. Prior to study, it was mixed with water under stirring to form lipid emulsified system 2.

The cytotoxicity of the various treatment groups (See Tables 4-6) were evaluated using a colorimetric MTS assay. The cell viability assay was performed according to the manufacturer's protocol with the Promega CellTitre 96 Aqueous MTS reagent (Madison, Wis., USA). Briefly, 7.5× $10^3$ cells were seeded in 96-well plates and were incubated overnight. The cells were treated with different concentrations of treatment groups followed by incubation for a period of 72 hours. At the end of the incubation period, the growth medium was removed followed by addition of 100 μl media consisting of 20% MTS and 1% of phenazine methosulfate (PMS) and the mixture was incubated for 2 h at 37° C. MTS is bio-reduced by the cells into formazan which could be measured using a microplate reader at 490 nm. Thus, the quantity of formazan measured by the absorbance is directly proportional to the number of living cells in culture. Using this data, $IC_{50}$ values were determined by Graph Pad Prism software (San Diego, Calif., USA). All analysis was performed in triplicate. The $IC_{50}$ concentration for various LOR and DES treatment groups is depicted in Table 4, Table 5 and Table 6.

TABLE 4

Enhancement in chemopreventive and therapeutic anticancer efficacy of antihistaminic drugs, LOR and DES when encapsulated in lipid emulsified system (Formulations 1, 2, 5, 6) in MIA-PaCa-2 pancreatic cancer cells (in vitro).

| Formulation/ Treatment Type | Composition | IC 50 (μM) | Enhancement of Efficacy Compared to LOR |
|---|---|---|---|
| Free drug | LOR (free) | 326.4 | |
| Formulation 1 | LOR Lipid Emulsified System 1 | 17.81 | ~18 X |
| Formulation 2 | LOR Lipid Emulsified System 2 | 7.248 | ~45 X |

| Formulation/ Treatment Type | Composition | IC 50 (μM) | Enhancement of Efficacy Compared to Desoratadine |
|---|---|---|---|
| Free drug | DES (free) | 267 | |
| Formulation 5 | DES Lipid Emulsified System 1 | 20.93 | ~13 X |
| Formulation 6 | DES Lipid Emulsified System 2 | 14.54 | ~18 X |

The lipid emulsified systems provide improved $IC_{50}$ values: LOR Lipid Emulsified System 1 and LOR Lipid Emulsified System 2, respectively, provide about 18× and 45× enhancement of efficacy compared to LOR (free). DES Lipid Emulsified System 1 and DES Lipid Emulsified System 2, respectively, provide about 13× and 18× enhancement of efficacy compared to DES (free).

TABLE 5

Enhancement in chemopreventive and therapeutic anticancer efficacy of antihistaminic
drug, LOR encapsulated in lipid emulsified system in combined with free SULFORAPHANE
(Formulations 3 and 4) in MIA-PaCa-2 pancreatic cancer cells (in vitro).

| Formulation/ Treatment Type | Composition | IC 50 ($\mu$M) | Enhancement of Efficacy Compared to | | | | |
|---|---|---|---|---|---|---|---|
| | | | LOR | Sulforaphane | LOR + Sulforaphane | LOR Lipid Emulsified System 1 | LOR Lipid Emulsified System 2 |
| Free drug | LOR (free) | 326.4 | | | | | |
| Free drug | Sulforaphane (free) | 92.18 | — | | | | |
| Free drug Combination | LOR + Sulforaphane | 4.6 | ~70 X | ~20 X | | | |
| Formulation 1 | LOR Lipid Emulsified System 1 | 17.81 | ~18 X | — | — | | |
| Formulation 2 | LOR Lipid Emulsified System 2 | 7.248 | ~45 X | — | — | — | |
| Formulation 3 | LOR Lipid Emulsified System 1 + Sulforaphane | 1.186 | ~275 X | ~78 X | ~4 X | ~15 X | — |
| Formulation 4 | LOR Lipid Emulsified System 2 + Sulforaphane | 0.639 | ~500 X | ~140 X | ~7 X | — | ~10 X |

The results show synergistic anticancer effects when the combination regimens are applied. LOR+Sulforaphane provides about 70× and 20× enhancement of efficacy compared to LOR (free) and Sulforaphane (free), respectively. LOR Lipid Emulsified System 1+Sulforaphane provides about 275× enhancement of efficacy compared to LOR (free), and LOR Lipid Emulsified System 2+Sulforaphane provides about 500× enhancement of efficacy compared to LOR (free).

DES Lipid Emulsified System 2+Sulforaphane provides about 900× enhancement of efficacy compared to DES (free).

Example 3: Additional Lipid Emulsified Systems

Lipid emulsified system 1 and 2 are described above For lipid emulsified system 1, drug, solid lipids in combination with one or more additional excipients from the class of

TABLE 6

Enhancement in chemopreventive and therapeutic anticancer efficacy of antihistaminic drug,
DES encapsulated in lipid emulsified system in combination with free SULFORAPHANE (Formulations 7
and 8) in MIA-PaCa-2 pancreatic cancer cells (in vitro).

| Formulation/ Treatment Type | Composition | IC 50 ($\mu$M) | Enhancement of Efficacy Compared to | | | | |
|---|---|---|---|---|---|---|---|
| | | | DES | Sulforaphane | DES + Sulforaphane | DES Lipid Emulsified System 1 | DES Lipid Emulsified System 2 |
| Free drug | DES (free) | 267 | | | | | |
| Free drug | Sulforaphane (free) | 92.18 | | | | | |
| Free drug Combination | DES + Sulforaphane | 8.705 | ~30 X | ~10 X | | | |
| Formulation 5 | DES Lipid Emulsified System 1 | 20.93 | 13X | — | — | | |
| Formulation 6 | DES Lipid Emulsified System 2 | 14.54 | 18 X | — | — | — | DES Lipid Emulsified System 2 |
| Formulation 7 | DES Lipid Emulsified System 1 + Sulforaphane | 0.534 | ~500 X | ~180 X | ~15 X | ~40 X | — |
| Formulation 8 | DES Lipid Emulsified System 2 + Sulforaphane | 0.289 | ~900 | ~300 X | ~35 X | — | ~50 X |

The results show synergistic anticancer effects when the combination regimens are applied. DES+Sulforaphane provides about 30× and 10× enhancement of efficacy compared to LOR (free) and Sulforaphane (free), respectively. DES Lipid Emulsified System 1+Sulforaphane provides about 500× enhancement of efficacy compared to LOR (free), and surface active agents and/or stabilizers were mixed in a specific ratio and the mixture was melted to achieve a homogeneous melt mix. Next, hot purified water was added dropwise under homogenization and the system was cooled to room temperature to achieve a lipid emulsified system 1 suspension. A specific concentration of cryoprotectant was added and the system was subjected to freeze-drying to achieve a dry powdered lipid emulsified system 1 formulation. This was stored as a dry lipid emulsified system 1. Prior to study, it was mixed with water under stirring to form lipid emulsified system 1.

For lipid emulsified system 2-6, drug, liquid lipid/s (oil/s) with one or more additional excipients from the class of surface active agents and/or stabilizers were mixed in varied ratio and the mixture was heated to achieve homogeneous mix. This was stored as a pre-concentrate lipid emulsified system 2-6. Prior to study, it was mixed with water under stirring to form lipid emulsified systems 2-6.

The characterization results of the LOR and DES lipid emulsified systemes developed are summarized in Table 7.

cancer cell lines were incubated with varied concentration of LOR and DES alone or encapsulated within lipid emulsified systems.

The cytotoxicity of the various treatment groups were evaluated using a colorimetric MTS assay. The cell viability assay was performed according to the manufacturer's protocol with the Promega CellTitre 96 Aqueous MTS reagent (Madison, Wis., USA). Briefly, 7.5×103 cells were seeded in 96-well plates and were incubated overnight. The cells were treated with different concentrations of treatment groups followed by incubation for a period of 72 hours. At the end of the incubation period, the growth medium was removed followed by addition of 100 µl media consisting of 20% MTS and 1% of phenazine methosulfate (PMS) and the mixture was incubated for 2 h at 37° C. MTS is bio-reduced

TABLE 7

Characterization of LOR and DES lipid emulsified systems

| Formulation | Size (nm) | PDI | Composition/Drug Loading |
|---|---|---|---|
| LOR formulations | | | |
| LOR Lipid Emulsified System 1 | 265 ± 33 | 0.2 | 20 mg LOR, 326.66 mg stearic acid, 326.66 mg Tween 80, 326.66 mg Transcutol ® HP, 50 mg mannitol; 2% w/w drug loading |
| LOR Lipid Emulsified System 2 | 95.13 ± 7.9 | 0.17 ± 0.04 | 20 mg LOR, 326.66 mg Capmul ® MCM grade specifically Capmul ® MCM C8- oil, 326.66 mg Tween ® 80, 326.66 mg Transcutol HP; 2% w/w drug loading |
| LOR Lipid Emulsified System 3 | 212.38 ± 24.33 | 0.26 ± 0.13 | 20 mg LOR, 245 mg Capmul ® MCM, 490 mg Tween ® 60, 245 mg PEG 200; 2% w/w drug loading |
| LOR Lipid Emulsified System 4 | 348.64 ± 37.28 | 0.31 ± 0.08 | 25 mg LOR, 195 mg oleic acid, 390 mg Tween ® 60, 390 mg Labrafil ® M2125CS; 2.5% w/w drug loading |
| LOR Lipid Emulsified System 5 | 186.39 ± 21.25 | 0.17 ± 0.06 | 25 mg LOR, 325 mg Capmul ® MCM 325 mg Tween ® 60, 325 mg PEG 400; 2.5% w/w drug loading |
| LOR Lipid Emulsified System 6 | 128.64 ± 18.58 | 0.23 ± 0.08 | 20 mg LOR, 245 mg Capmul ® GMO50, 490 mg Tween ® 80, 245 mg PEG 400; 2% w/w drug loading |
| DES formulations | | | |
| DES Lipid Emulsified System 1 | 286 ± 49 | 0.2 | 20 mg DES, 326.66 mg stearic acid, 326.66 mg Tween 80, 326.66 mg Transcutol ® HP, 50 mg mannitol; 2% w/w drug loading |
| DES Lipid Emulsified System 2 | 108.29 ± 9.26 | 0.19 ± 0.07 | 20 mg DES, 326.66 mg Capmul ® MCM grade specifically Capmul ® MCM C8- oil, 326.66 mg Tween ® 80, 326.66 mg Transcutol HP; 2% w/w drug loading |
| DES Lipid Emulsified System 3 | 424.46 ± 32.98 | 0.35 ± 0.09 | 20 mg DES, 245 mg Capmul ® MCM, 490 mg Tween ® 60, 245 mg PEG 200; 2% w/w drug loading |
| DES Lipid Emulsified System 4 | 310.24 ± 49.76 | 0.28 ± 0.06 | 25 mg DES, 195 mg oleic acid, 390 mg Tween ® 60, 390 mg Labrafil ® M2125CS; 2.5% w/w drug loading |
| DES Lipid Emulsified System 5 | 232.64 ± 36.22 | 0.22 ± 0.12 | 25 mg DES, 325 mg Capmul ® MCM, 325 mg Tween ® 60, 325 mg PEG 400; 2.5% w/w drug loading |
| DES Lipid Emulsified System 6 | 167.38 ± 28.39 | 0.36 ± 0.16 | 20 mg DES, 245 mg Capmul ® GMO50, 490 mg Tween ® 80, 245 mg PEG 400; 2% w/w drug loading |

The lipid emulsified systems were observed to be stable with size less than 500 nm.

Example 4: Cytotoxicity Studies with Additional Lipid Emulsified Systems

An in vitro study to determine $IC_{50}$ (inhibitory concentration to kill 50% of cancer cells) in pancreatic cancer cell lines was performed. MIA-PaCa-2 and Panc-1 pancreatic by the cells into formazan which could be measured using a microplate reader at 490 nm. Thus, the quantity of formazan measured by the absorbance is directly proportional to the number of living cells in culture. Using this data, IC50 values were determined by Graph Pad Prism software (San Diego, Calif., USA). The results are summarized in Table 8 and Table 9.

The cytotoxicity of the various treatment groups were evaluated using the colorimetric MTS assay. A lower $IC_{50}$ concentration implies higher potency and hence higher chemopreventive/therapeutic efficacy against cancer.

TABLE 8

Enhancement in chemopreventive and therapeutic anticancer efficacy of antihistaminic drugs, LOR and DES when encapsulated in lipid emulsified system in MIA-PaCa-2 pancreatic cancer cells (in vitro).

| Formulation Type | Composition | $IC_{50}$ (μM) |
|---|---|---|
| Free drug | LOR (free) | 326.4 |
| Formulation | LOR Lipid Emulsified System 1 | 17.81 |
| | LOR Lipid Emulsified System 2 | 7.248 |
| | LOR Lipid Emulsified System 3 | 23.25 |
| | LOR Lipid Emulsified System 4 | 14.29 |
| | LOR Lipid Emulsified System 5 | 10.28 |
| | LOR Lipid Emulsified System 6 | 28.29 |
| Free drug | DES (free) | 267 |
| Formulation | DES Lipid Emulsified System 1 | 20.93 |
| | DES Lipid Emulsified System 2 | 14.54 |
| | DES Lipid Emulsified System 3 | 42.36 |
| | DES Lipid Emulsified System 4 | 31.28 |
| | DES Lipid Emulsified System 5 | 24.43 |
| | DES Lipid Emulsified System 6 | 53.49 |

An enhancement of cytotoxic efficacy is seen in all lipid emulsified system for both LOR and DES relative to the free drug. LOR Lipid Emulsified System 2 shows an enhancement of about 45×.

TABLE 9

Enhancement in chemopreventive and therapeutic anticancer efficacy of antihistaminic drugs, LOR and DES when encapsulated in lipid emulsified system in Panc-1 pancreatic cancer cells (in vitro).

| Formulation Type | Composition | $IC_{50}$ (μM) |
|---|---|---|
| Free drug | LOR (free) | 356.8 |
| Formulation | LOR Lipid Emulsified System 1 | 38.52 |
| | LOR Lipid Emulsified System 2 | 10.90 |
| | LOR Lipid Emulsified System 3 | 51.76 |
| | LOR Lipid Emulsified System 4 | 32.74 |
| | LOR Lipid Emulsified System 5 | 24.78 |
| | LOR Lipid Emulsified System 6 | 56.33 |
| Free drug | DES (free) | 249.88 |
| Formulation | DES Lipid Emulsified System 1 | 27.36 |
| | DES Lipid Emulsified System 2 | 15.38 |
| | DES Lipid Emulsified System 3 | 32.29 |
| | DES Lipid Emulsified System 4 | 20.29 |
| | DES Lipid Emulsified System 5 | 43.28 |
| | DES Lipid Emulsified System 6 | 48.63 |

An enhancement of cytotoxic efficacy is seen in all lipid emulsified system for both LOR and DES relative to the free drug. LOR Lipid Emulsified System 2 shows an enhancement of about 33×.

Significant enhancement in the inhibitory action on pancreatic cancer cell lines as a result of encapsulation in lipid emulsified systems offers enhanced chemopreventative efficacy and enhanced therapeutic efficacy, compared to the free drug. Based on the above results, Lipid Emulsified Systems 1 and 2 were selected for further investigation.

Example 5: Cytotoxicity Studies with Free Sulforaphane

Additional cytotoxicity studies with free sulforaphane were performed in Panc-1 pancreatic cancer cells. The cell viability assay was performed according to the manufacturer's protocol with the Promega Cell Titre 96 Aqueous MTS reagent (Madison, Wis., USA). Briefly, 7.5×10³ cells were seeded in 96-well plates and were incubated overnight. The cells were treated with different concentrations of treatment groups followed by incubation for a period of 72 h. At the end of the incubation period, the growth medium was removed followed by addition of 100 μl media consisting of 20% MTS and 1% of phenazine methosulfate (PMS) and the mixture was incubated for 2 h at 37° C. MTS is bio-reduced by the cells into formazan which could be measured using a microplate reader at 490 nm. Thus, the quantity of formazan measured by the absorbance is directly proportional to the number of living cells in culture. Using this data, $IC_{50}$ values were determined by Graph Pad Prism software (San Diego, Calif., USA). The results in Panc-1 pancreatic cancer cells are shown in Tables 10 and 11.

TABLE 10

Enhancement in chemopreventive and therapeutic anticancer efficacy of antihistaminic drug, LOR encapsulated in lipid emulsified system in combination with free Sulforaphane in Panc-1 pancreatic cancer cells (in vitro).

| Formulation/Treatment Type | Composition | $IC_{50}$ (μM) |
|---|---|---|
| Free drug | LOR (free) | 356.8 |
| Free drug | Sulforaphane (free) | 99.59 |
| Free drug Combination | LOR + Sulforaphane | 9.51 |
| Formulation | LOR Lipid Emulsified System 1 | 38.52 |
|  | LOR Lipid Emulsified System 2 | 10.90 |
|  | LOR Lipid Emulsified System 1 + Sulforaphane | 1.78 |
|  | LOR Lipid Emulsified System 2 + Sulforaphane | 0.82 |

TABLE 11

Enhancement in chemopreventive and therapeutic anticancer efficacy of antihistaminic drug, DES encapsulated in lipid emulsified system in combination with free Sulforaphane in Panc-1 pancreatic cancer cells (in vitro).

| Formulation/Treatment Type | Composition | $IC_{50}$ (μM) |
|---|---|---|
| Free drug | DES (free) | 249.88 |
| Free drug | Sulforaphane (free) | 99.59 |
| Free drug Combination | DES + Sulforaphane | 14.73 |
| Formulation | DES Lipid Emulsified System 1 | 27.36 |
|  | DES Lipid Emulsified System 2 | 15.38 |
|  | DES Lipid Emulsified System 1 + Sulforaphane | 1.037 |
|  | DES Lipid Emulsified System 2 + Sulforaphane | 0.354 |

The results once again show synergistic anticancer effects when the combination regimens are applied. LOR+Sulforaphane provides about 38× and 10× enhancement of efficacy compared to LOR (free) and Sulforaphane (free), respectively. LOR Lipid Emulsified System 1+Sulforaphane provides about 200× enhancement of efficacy compared to LOR (free), and LOR Lipid Emulsified System 2+Sulforaphane provides about 435× enhancement of efficacy compared to LOR (free). DES+Sulforaphane provides about 17× and 7× enhancement of efficacy compared to LOR (free) and Sulforaphane (free), respectively. DES Lipid Emulsified System 1+Sulforaphane provides about 240× enhancement of efficacy compared to LOR (free), and DES Lipid Emulsified System 2+Sulforaphane provides about 706× enhancement of efficacy compared to DES (free).

Example 6: Relative Ratios of Antihistamine to Sulforaphane

Figure 5:
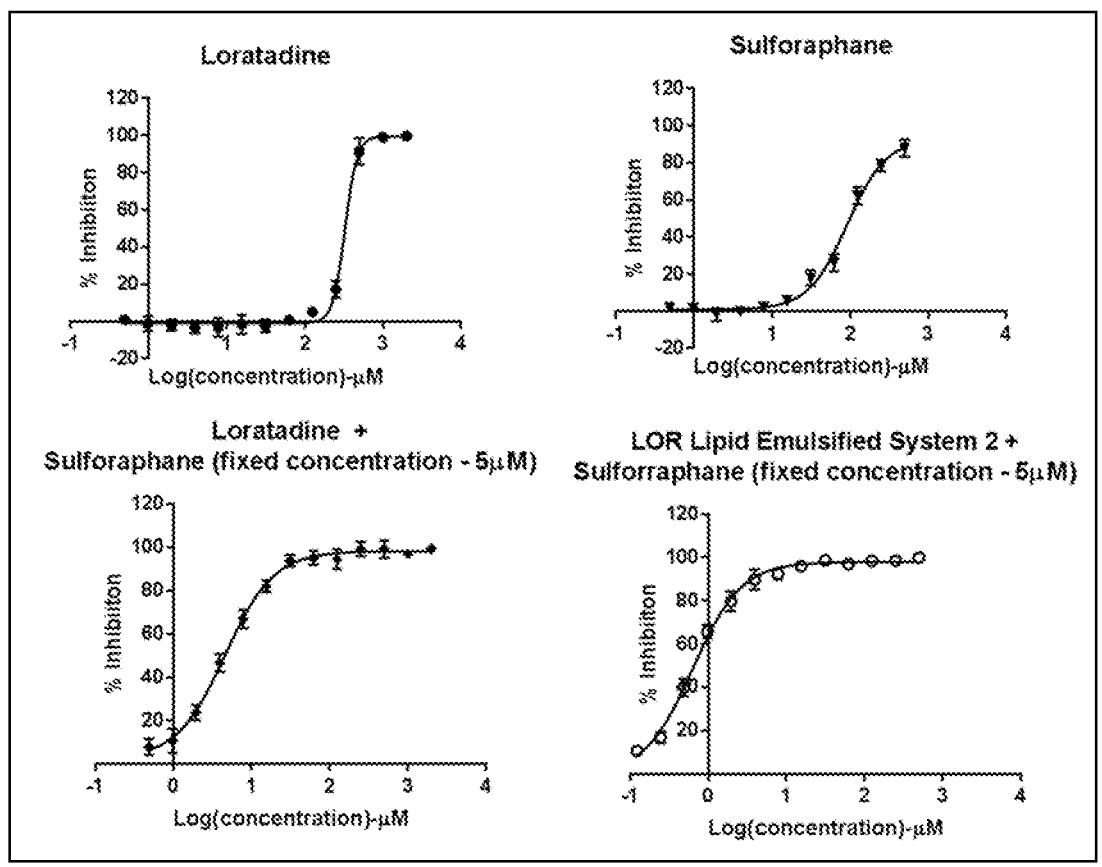
FIG. 5 shows dose-inhibition response curves for LOR free form or encapsulated in lipid emulsified system 2 in combination with free Sulforaphane in Mia PaCa 2 pancreatic cancer cells (in vitro), showing chemopreventive and therapeutic anticancer efficacy.
Figure 6:
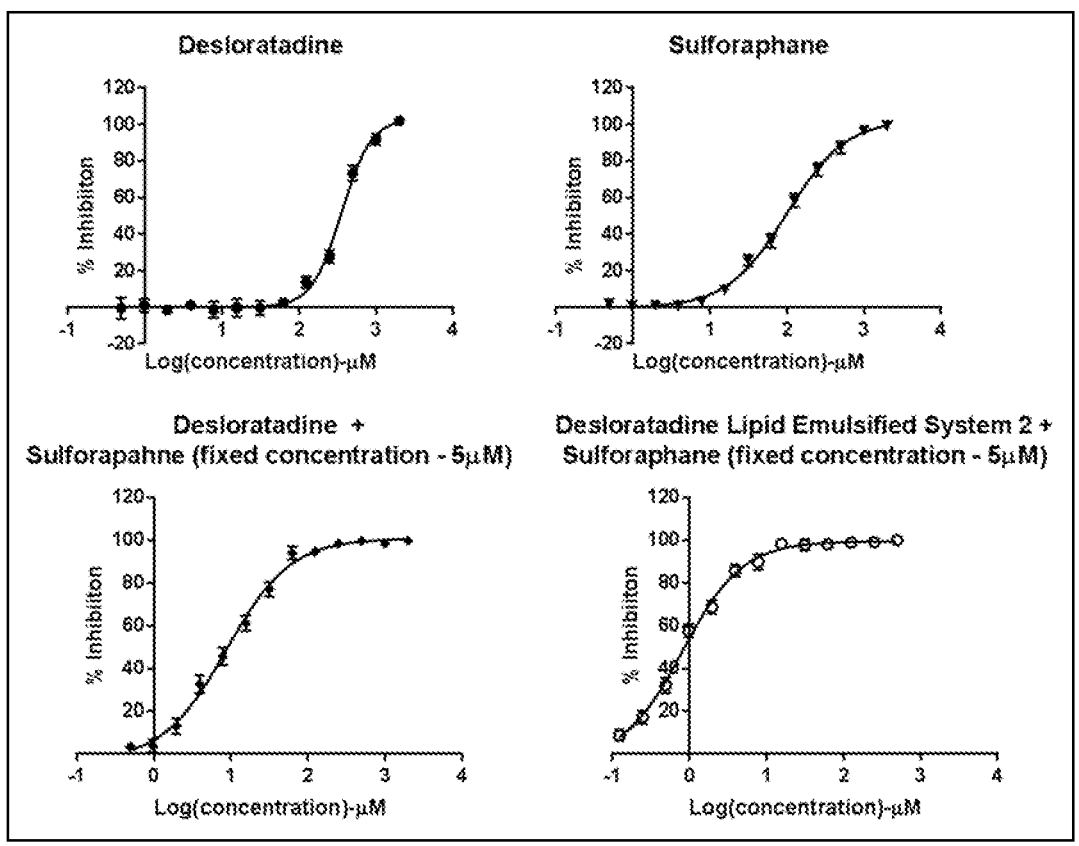
FIG. 6 shows dose-inhibition response curves for DES free form or encapsulated in lipid emulsified system 2 in combination with free Sulforaphane in Mia PaCa 2 pancreatic cancer cells (in vitro), showing chemopreventive and therapeutic anticancer efficacy.

Cytotoxicity was evaluated in Mia PaCa 2 pancreatic cancer cells using the colorimetric MTS assay, as described above. Cancer cell lines were incubated with combination of fixed concentration of free Sulforaphane (5 μM) with varied concentration of LOR/DES within the range of 0.5-2000 μM. This reflects a relative ratio of sulforaphane to LOR/DES of from 1:0.1 to 1:400. Similarly, cancer cell lines were incubated with combination of fixed concentration of free Sulforaphane (5 μM) with varied concentration of LOR/DES lipid emulsified system 2 within the range of 0.1-500 μM. This reflects a relative ratio of sulforaphane to LOR/DES of from 1:0.02 to 1:100. The inhibition response curves are provided in FIG. 5 and FIG. 6.

The Sulforaphane/LOR and Sulforaphane/DES free drug combinations showed inhibitory response when Mia PaCa-2 cell line was treated at the relative ratio of sulforaphane to LOR/DES 1:0.1 to 1:400. The Sulforaphane/LOR lipid emulsified System 2 and Sulforaphane/DES lipid emulsified System 2 combinations showed inhibitory response when Mia PaCa-2 cell line was treated at the relative ratio of sulforaphane to LOR/DES 1:0.02 to 1:100.

The Sulforaphane/LOR and Sulforaphane/DES free drug combinations did not show any significant cell inhibition at the concentration of 125 μM and free drug Sulforaphane did not show any significant cell inhibition at the concentration of 5 μM. a fixed dose combination of sulforaphane and LOR/DES at ratio of 1:25 was used for further studies. The rationale here is to use drug concentration that does not elicit ant inhibitory response when used alone but shows efficacy when combined together. A fixed dose combination of Sulforaphane with LOR or DES at ratio of 1:25 was used for further studies. These drug concentrations do not elicit any inhibitory response when used alone, but shows efficacy when combined together. Taken together with the results in Examples 2 and 5, these results further support safety, efficacy and synergism.

Example 7: Pharmacokinetic Studies

Lipid emulsified system 2 was selected optimal for further investigations as it showed the highest chemoprevention and treatment efficacy against pancreatic cancer cell lines. Preclinical in vivo pharmacokinetic studies were performed in Sprague Dawley rats to confirm the hypothesis of bioavailability enhancement using the lipid emulsified formulation strategy. LOR Lipid Emulsified System 2 with Sulforaphane and DES Lipid Emulsified System 2 with Sulforaphane were administered orally and the resulting bioavailability was compared against the plain drug combination LOR-Sulforaphane and DES-Sulforaphane as controls, respectively.

For this study, 30 pre-cannulated Sprague Dawley rats were divided into 5 groups at random (6 rats per group), and each group received the single dose treatment as described in the Table 12 via oral gavage. The blood was drawn at specified time points of 30 min, 1 h, 2 h, 6 h, 12 h, 24 h and 48 h and the concentrations of LOR, DES, Sulforaphane were measured using a validated LCMS method.

TABLE 12

Pharmacokinetic study protocol

| Treatment | Dose |
|---|---|
| Blank Lipid Emulsified System 2 | Volume equivalent to dose volume of LOR/ DES Lipid Emulsified System 2 |
| LOR + Sulforaphane | 4 mg/kg + 0.16 mg/kg |
| LOR Lipid Emulsified System 2 + Sulforaphane | 4 mg/kg + 0.16 mg/kg |
| DES + Sulforaphane | 4 mg/kg + 0.16 mg/kg |
| DES Lipid Emulsified System 2 + Sulforaphane | 4 mg/kg + 0.16 mg/kg |

Figure 7:
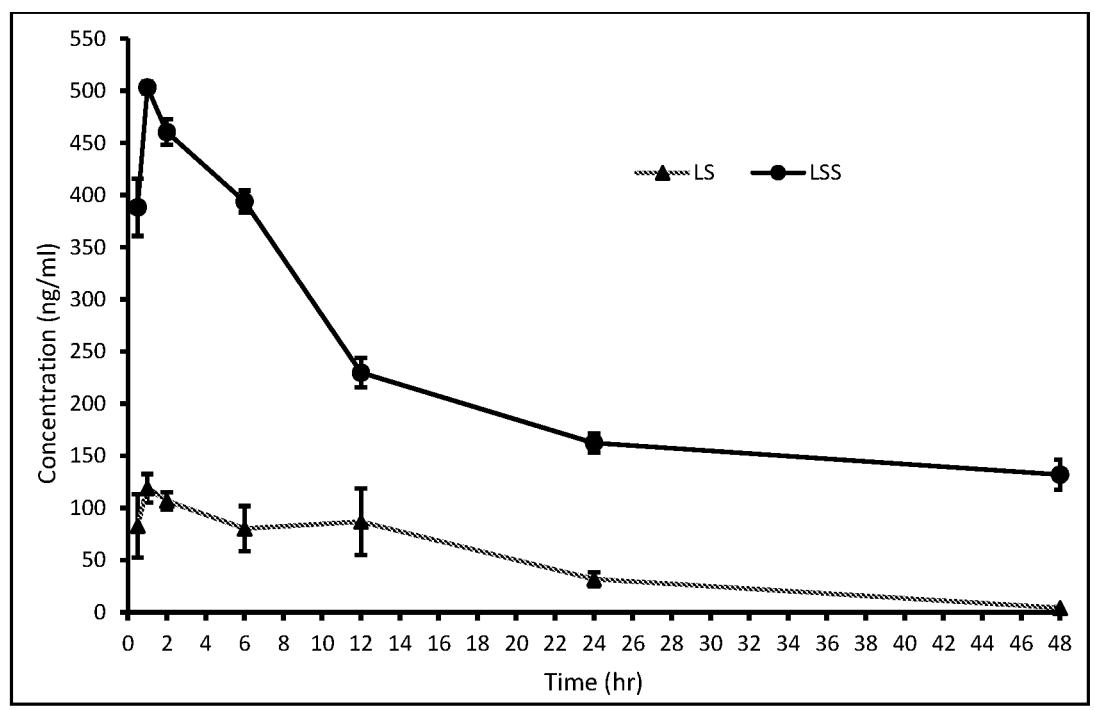
FIG. 7 shows pharmacokinetic estimation of LOR in Sprague Dawley rats (n=6) following treatment with LOR+ Sulforaphane (LS), LOR Lipid Emulsified System 2+Sulforaphane (LSS).
Figure 8:
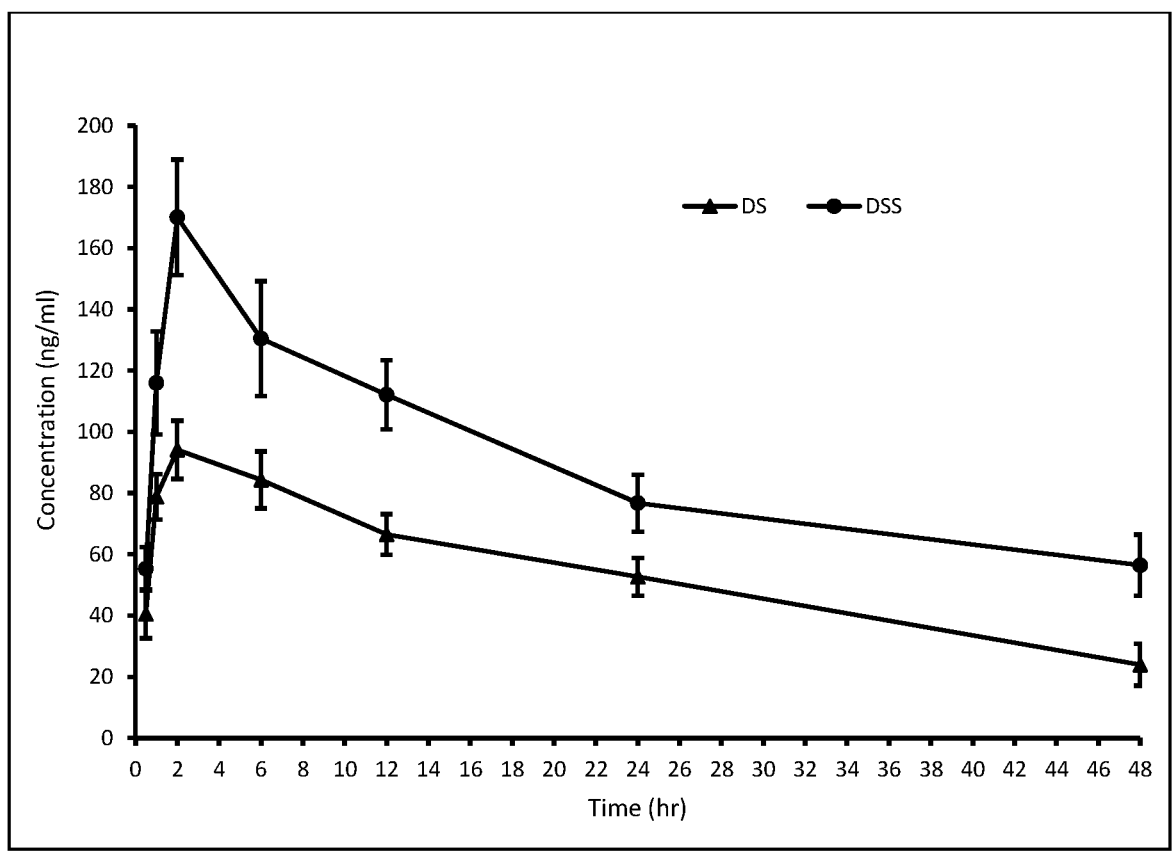
FIG. 8 shows pharmacokinetic estimation of DES in Sprague Dawley rats (n=6) following treatment with DES+ Sulforaphane (DS), and DES Lipid Emulsified System 2+Sulforaphane (DSS)

The in vivo pharmacokinetic study results for LOR and DES are depicted in FIG. 7 and FIG. 8, respectively and the comparative data is summarized in Table 13. The results confirmed that the bioavailability and $C_{max}$ of LOR increased 5× and 4× when administered as Lipid Emulsified System 2. Similarly, the bioavailability and $C_{max}$ of DES increased 2× when administered as Lipid Emulsified System 2. The studies confirmed that formulating LOR and DES as a lipid emulsified system leads to significant enhancement of in vivo bioavailability allowing for increased efficacy for chemoprevention and treatment.

TABLE 13

Pharmacokinetics of LOR, DES, and Sulforaphane in rats (n = 6, Mean ± SD) following treatment with LOR + Sulforaphane (LS), LOR Lipid Emulsified System 2 + Sulforaphane (LSS), DES + Sulforaphane (DS), and DES Lipid Emulsified System 2 + Sulforaphane (DSS)

| Compound | Parameter | Dose | | | |
|---|---|---|---|---|---|
| | | LS | LSS | DS | DSS |
| LOR | $AUC_{0-t}$ (ng · h/mL) | 2203.2 ± 293.7 | 10266.1 ± 250.0 | — | — |
| | $AUC_{0-\infty}$ (ng · h/mL) | 2258.7 ± 308.5 | 20274.8 ± 3711.0 | — | — |
| | CL/F (L/h/kg) | 1.80 ± 0.24 | 0.20 ± 0.04 | — | — |
| | $V_d$/F (L/kg) | 23.9 ± 2.5 | 14.4 ± 1.6 | — | — |
| | $K_e$ ($h^{-1}$) | 0.075 ± 0.004 | 0.015 ± 0.005 | — | — |
| | $t_{1/2}$ (h) | 9.26 ± 0.47 | 51.3 ± 14.2 | — | — |
| | $T_{max}$ (h) | 1.33 ± 0.52 | 1 | — | — |
| | $C_{max}$ (ng/ml) | 120.9 ± 10.5 | 503.2 ± 5.8 | — | — |
| DES | $AUC_{0-t}$ (ng · h/mL) | — | — | 2570.5 ± 170.0 | 4259.6 ± 128.5 |
| | $AUC_{0-\infty}$ (ng · h/mL) | — | — | 3443.2 ± 552.0 | 7275.4 ± 1173.4 |
| | CL/F (L/h/kg) | — | — | 1.19 ± 0.19 | 0.56 ± 0.08 |
| | $V_d$/F (L/kg) | — | — | 40.1 ± 3.8 | 28.4 ± 2.6 |
| | $K_e$ ($h^{-1}$) | — | — | 0.030 ± 0.007 | 0.020 ± 0.004 |
| | $t_{1/2}$ (h) | — | — | 24.1 ± 5.4 | 36.1 ± 8.4 |
| | $T_{max}$ (h) | — | — | 2.67 ± 1.63 | 2.67 ± 1.63 |
| | $C_{max}$ (ng/ml) | — | — | 96.1 ± 7.9 | 171.4 ± 17.8 |
| Sulforaphane | $AUC_{0-t}$ (ng · h/mL) | 313.0 ± 27.6 | 374.7 ± 17.8 | 3245.0 ± 194.7 | 3942.1 ± 287.7 |
| | $AUC_{0-\infty}$ (ng · h/mL) | 348.8 ± 47.0 | 417.0 ± 67.5 | 3337.4 ± 232.7 | 4058.5 ± 273.1 |
| | CL/F (L/h/kg) | 0.46 ± 0.06 | 0.39 ± 0.05 | 0.048 ± 0.004 | 0.040 ± 0.003 |
| | $V_d$/F (L/kg) | 3.16 ± 0.45 | 3.11 ± 0.82 | 0.32 ± 0.04 | 0.31 ± 0.02 |
| | $K_e$ ($h^{-1}$) | 0.151 ± 0.032 | 0.135 ± 0.044 | 0.152 ± 0.024 | 0.129 ± 0.013 |
| | $t_{1/2}$ (h) | 4.83 ± 1.31 | 5.77 ± 2.48 | 4.65 ± 0.71 | 5.42 ± 0.52 |
| | $T_{max}$ (h) | 0.83 ± 0.26 | 0.92 ± 0.20 | 0.92 ± 0.20 | 0.83 ± 0.26 |

Example 9: Combinations with Gemcitabine

A study to determine $IC_{50}$ in in vitro cell line cultures of pancreatic cancer cell lines was performed. MIA-PaCa-2 and Panc-1 pancreatic cancer cell lines were incubated with varied concentrations of Gemcitabine alone or in addition to the fixed concentration of LOR/DES free drug or as lipid emulsified system 2 (125 µM) with a fixed concentration of free Sulforaphane (5 µM). Cytotoxicity was evaluated using the colorometric MTS assay. The cell viability assay was performed according to the manufacturer's protocol with the Promega Cell Titre 96 Aqueous MTS reagent (Madison, Wis., USA). Briefly, $7.5 \times 10^6$ cells were seeded in 96-well plates and were incubated overnight. The cells were treated with different concentrations of treatment groups followed by incubation for a period of 72 h. At the end of the incubation period, the growth medium was removed followed by addition of 100 µl media consisting of 20% MTS and 1% of phenazine methosulfate (PMS) and the mixture was incubated for 2 h at 37° C. MTS is bio-reduced by the cells into formazan which could be measured using a microplate reader at 490 nm. Thus, the quantity of formazan measured by the absorbance is directly proportional to the number of living cells in culture. Using this data, $IC_{50}$ values were determined by Graph Pad Prism software (San Diego, Calif., USA). The results are provided in Tables 14-17.

TABLE 14

Enhancement in chemopreventive and therapeutic anticancer efficacy of Gemcitabine when combined with antihistaminic drug, LOR encapsulated in lipid emulsified system in combination with free Sulforaphane in MIA-PaCa-2 pancreatic cancer cells (in vitro).

| Formulation/Treatment Type | Composition | $IC_{50}$ (µM) |
|---|---|---|
| Free Drug | Gemcitabine | 692.47 |
| Free Drug Combination | Gemcitabine + LOR + Sulforaphane | 533.24 |
| Formulation | Gemcitabine + LOR Lipid Emulsified System 2 + Sulforaphane | 286.39 |

TABLE 15

Enhancement in chemopreventive and therapeutic anticancer efficacy of Gemcitabine when combined with antihistaminic drug, DES encapsulated in lipid emulsified system in combination with free Sulforaphane in MIA-PaCa-2 pancreatic cancer cells (in vitro).

| Formulation/Treatment Type | Composition | $IC_{50}$ (µM) |
|---|---|---|
| Free Drug | Gemcitabine | 692.47 |
| Free Drug Combination | Gemcitabine + DES + Sulforaphane | 486.38 |
| Formulation | Gemcitabine + DES Lipid Emulsified System 2 + Sulforaphane | 239.64 |

TABLE 16

Enhancement in chemopreventive and therapeutic anticancer efficacy of Gemcitabine when combined with antihistaminic drug, LOR encapsulated in lipid emulsified system in combination with free Sulforaphane in Panc-1 pancreatic cancer cells (in vitro).

| Formulation/Treatment Type | Composition | $IC_{50}$ (µM) |
|---|---|---|
| Free Drug | Gemcitabine | 538.72 |
| Free Drug Combination | Gemcitabine + LOR + Sulforaphane | 367.44 |
| Formulation | Gemcitabine + LOR Lipid Emulsified System 2 + Sulforaphane | 286.98 |

TABLE 17

Enhancement in chemopreventive and therapeutic anticancer efficacy of Gemcitabine when combined with antihistaminic drug, DES encapsulated in lipid emulsified system in combination with free Sulforaphane in Panc-1 pancreatic cancer cells (in vitro).

| Formulation/Treatment Type | Composition | $IC_{50}$ (µM) |
| --- | --- | --- |
| Free Drug | Gemcitabine | 538.72 |
| Free Drug Combination | Gemcitabine + DES + Sulforaphane | 332.58 |
| Formulation | Gemcitabine + DES Lipid Emulsified System 2 + Sulforaphane | 186.39 |

The in vitro cytotoxicity assay evaluated the therapeutic effects of gemcitabine in combination with LOR/DES lipid emulsified systems with Sulforaphane on Panc-1 and MIA PaCa-2 cell lines. The results showed synergistic anticancer effects when treated with the combination regimens. The combination with lipid emulsified system 2 and sulforaphane provides nearly 2× to 3× increased efficacy compared to gemcitabine alone. Hence, these cell lines are more sensitive to gemcitabine with the combination treatment. The increased sensitivity of these pancreatic cancer cell lines to gemcitabine also allows for the use of the combination treatment to be used against gemcitabine resistant cancers.

Example 10: Combinations with Paclitaxel

A study to determine $IC_{50}$ in in vitro cell line cultures of pancreatic cancer cell lines was performed. MIA-PaCa-2 and Panc-1 pancreatic cancer cell lines were incubated with varied concentrations of Paclitaxel alone or in addition to the fixed concentration of LOR/DES free drug or as lipid emulsified system 2 (125 µM) with a fixed concentration of free Sulforaphane (5 µM). Cytotoxicity was evaluated using the colorometric MTS assay. The cell viability assay was performed according to the manufacturer's protocol with the Promega Cell Titre 96 Aqueous MTS reagent (Madison, Wis., USA). Briefly, $7.5 \times 10^6$ cells were seeded in 96-well plates and were incubated overnight. The cells were treated with different concentrations of treatment groups followed by incubation for a period of 72 h. At the end of the incubation period, the growth medium was removed followed by addition of 100 µl media consisting of 20% MTS and 1% of phenazine methosulfate (PMS) and the mixture was incubated for 2 h at 37° C. MTS is bio-reduced by the cells into formazan which could be measured using a microplate reader at 490 nm. Thus, the quantity of formazan measured by the absorbance is directly proportional to the number of living cells in culture. Using this data, $IC_{50}$ values were determined by Graph Pad Prism software (San Diego, Calif., USA). The results are provided in Tables 18-21.

TABLE 18

Enhancement in chemopreventive and therapeutic anticancer efficacy of Paclitaxel when combined with antihistaminic drug, LOR encapsulated in lipid emulsified system in combination with free Sulforaphane in MIA-PaCa-2 pancreatic cancer cells (in vitro).

| Formulation/Treatment Type | Composition | $IC_{50}$ (µM) |
| --- | --- | --- |
| Free Drug | Paclitaxel | 1.96 |
| Free Drug Combination | Paclitaxel + LOR + Sulforaphane | 1.41 |
| Formulation | Paclitaxel + LOR Lipid Emulsified System 2 + Sulforaphane | 1.08 |

TABLE 19

Enhancement in chemopreventive and therapeutic anticancer efficacy of Paclitaxel when combined with antihistaminic drug, DES encapsulated in lipid emulsified system in combination with free Sulforaphane in MIA-PaCa-2 pancreatic cancer cells (in vitro).

| Formulation/Treatment Type | Composition | $IC_{50}$ (µM) |
| --- | --- | --- |
| Free Drug | Paclitaxel | 1.96 |
| Free Drug Combination | Paclitaxel + DES + Sulforaphane | 1.58 |
| Formulation | Paclitaxel + DES Lipid Emulsified System 2 + Sulforaphane | 1.16 |

TABLE 20

Enhancement in chemopreventive and therapeutic anticancer efficacy of Paclitaxel when combined with antihistaminic drug, LOR encapsulated in lipid emulsified system in combination with free Sulforaphane in Panc-1 pancreatic cancer cells (in vitro).

| Formulation/Treatment Type | Composition | $IC_{50}$ (μM) |
|---|---|---|
| Free Drug | Paclitaxel | 2.33 |
| Free Drug Combination | Paclitaxel + LOR + Sulforaphane | 1.81 |
| Formulation | Paclitaxel + LOR Lipid Emulsified System 2 + Sulforaphane | 1.37 |

TABLE 21

Enhancement in chemopreventive and therapeutic anticancer efficacy of Paclitaxel when combined with antihistaminic drug, DES encapsulated in lipid emulsified system in combination with free Sulforaphane in Panc-1 pancreatic cancer cells (in vitro).

| Formulation/Treatment Type | Composition | $IC_{50}$ (μM) |
|---|---|---|
| Free Drug | Paclitaxel | 2.33 |
| Free Drug Combination | Paclitaxel + DES + Sulforaphane | 1.94 |
| Formulation | Paclitaxel + DES Lipid Emulsified System 2 + Sulforaphane | 1.29 |

The in vitro cytotoxicity assay evaluated the therapeutic effects of paclitaxel in combination with LOR/DES lipid emulsified systems with Sulforaphane on Panc-1 and MIA PaCa-2 cell lines. The results showed synergistic anticancer effects when treated with the combination regimens. The combination with lipid emulsified system 2 and sulforaphane provides nearly 2× increased efficacy compared to paclitaxel alone. Hence, these cell lines are more sensitive to paclitaxel with the combination treatment. The increased sensitivity of these pancreatic cancer cell lines to paclitaxel also allows for the use of the combination treatment to be used against paclitaxel resistant cancers.

What is claimed:

1. A method of treating cancer in an individual in need thereof, comprising the steps of:
   (A) administering to the individual an effective amount of a chemotherapeutic agent;
   (B) administering to the individual an effective amount of a pharmaceutical composition comprising:
      (i) a lipid emulsified system comprising:
         (a) a lipid;
         (b) a surfactant;
         (c) an antihistamine selected from loratadine or desloratadine
         wherein the average particle size of the lipid emulsified system is less than or equal to about 500 nm,
         wherein the ratio of (a) the lipid to (c) the antihistamine is about 4:1 to about 20: 1, and
         the ratio of (a) the lipid to (b) the surfactant is from about 1:1 to about 1:4;
      and
      (ii) a pharmaceutically acceptable excipient,
         wherein the cancer is selected from breast cancer, melanoma, ovarian cancer, lung cancer, pancreatic cancer, myeloma cancer, colorectal cancer, renal cancer, lymphoma and colon cancer.

2. The method of claim 1, wherein the chemotherapeutic agent is selected from the group consisting of gemcitabine, paclitaxel, capecitabine, 5-fluorouracil, irinotecan, erlotinib, docetaxel, oxaliplatin, celecoxib, olaparib, tamoxifen, and doxorubicin.

3. The method of claim 1, wherein the lipid emulsified system further comprises at least one of:
   (d) a stabilizer; and
   (e) a cryoprotectant.

4. The method of claim 1, wherein the lipid is a $C_6$ to $C_{22}$ saturated or unsaturated fatty acid, or a mono-, di-, or tri-glyceride of $C_5$ to $C_{22}$ saturated or unsaturated fatty acids, or combinations thereof.

5. The method of claim 1, wherein the lipid comprising the lipid emulsified system is selected from the group consisting of stearic acid, oleic acid, glyceryl caprylate-caprate, and glyceryl monooleate, glyceryl dibehenate and combinations thereof.

6. The method of claim 1, wherein the lipid is selected from the group consisting of stearic acid, glycerol caprylate/caprate, glyceryl caprylate, glyceryl oleate, and combinations thereof.

7. The method of claim 1, wherein the surfactant is a nonionic surfactant selected from a polyoxypropylene-polyoxyethylene copolymer, a polyoxyethylene sorbitan ester of saturated or unsaturated fatty acids, a glyceryl ester of polyethylene glycols, or combinations thereof.

8. The method of claim 1, wherein the surfactant is selected from the group consisting of ethylene oxide/propylene oxide copolymer, polyoxyethylene sorbitan monostearate, polysorbate 80, corn oil PEG-6 esters consisting of mono-, di- and triglycerides and PEG-6 (MW 300) mono- and diesters of linoleic (C18:2) acid, and combinations thereof.

9. The method of claim 3, wherein the stabilizer is a diethylene glycol monoethyl ether or a polyethylene glycol.

10. The method of claim 9, wherein the stabilizer is selected from the group consisting of diethylene glycol monoethyl ether, PEG 200, and PEG400.

11. The method of claim 3, wherein the cryoprotectant is a sugar or sugar alcohol.

12. The method of claim 3, wherein the cryoprotectant is mannitol.

13. The method of claim 1, wherein the lipid emulsified system has a polydispersity index of particle size distribution of 0.2 or less.

14. The method of claim 13, wherein the average particle size of the lipid emulsified system is about 300 nm.

15. The method of claim 1, wherein the treating cancer in an individual in need thereof comprises killing cancer cells.

16. The method of claim 1, wherein the pharmaceutical composition of step (B) further comprises sulforaphane.

17. The method of claim 1, wherein steps (A) and (B) are performed concurrently.

\* \* \* \* \*